(12) United States Patent
Gorton et al.

(10) Patent No.: US 11,710,235 B2
(45) Date of Patent: Jul. 25, 2023

(54) SYSTEMS AND METHODS FOR PROCESSING ELECTRONIC IMAGES OF SLIDES FOR A DIGITAL PATHOLOGY WORKFLOW

(71) Applicant: PAIGE.AI, Inc., New York, NY (US)

(72) Inventors: Danielle Gorton, Beacon, NY (US); Patricia Raciti, New York, NY (US); Jillian Sue, New York, NY (US); Razik Yousfi, Brooklyn, NY (US)

(73) Assignee: Paige.AI, Inc., New York, NY (US)

( * ) Notice: Subject to any disclaimer, the term of this patent is extended or adjusted under 35 U.S.C. 154(b) by 0 days.

(21) Appl. No.: 17/552,438

(22) Filed: Dec. 16, 2021

(65) Prior Publication Data

US 2022/0198666 A1 Jun. 23, 2022

Related U.S. Application Data

(60) Provisional application No. 63/127,846, filed on Dec. 18, 2020.

(51) Int. Cl.
*G06K 9/00* (2022.01)
*G06T 7/00* (2017.01)
(Continued)

(52) U.S. Cl.
CPC ............ *G06T 7/0014* (2013.01); *G06T 11/60* (2013.01); *G06V 10/12* (2022.01); *G06V 10/25* (2022.01);
(Continued)

(58) Field of Classification Search
CPC ........ G06T 7/0014; G06T 2207/30024; G06V 10/25; G06V 10/12; G06V 10/7715; G06V 2201/03
See application file for complete search history.

(56) References Cited

U.S. PATENT DOCUMENTS

2019/0156159 A1 5/2019 Kopparapu
2019/0164287 A1* 5/2019 Gregson ............... G06T 7/0014
(Continued)

FOREIGN PATENT DOCUMENTS

EP 2535757 A1 * 12/2012 .......... G02B 21/367
EP 3486835 A1 5/2019
(Continued)

OTHER PUBLICATIONS

Moxley-Wyles Benjamin et al: "Artificial intelligence in pathology: an overview", Diagnostic Histopathology, Elsevier, Amsterdam, NL, vol. 26, No. 11, Sep. 10, 2020 (Sep. 10, 2020), pp. 513-520, XP086313555, ISSN: 1756-2317, DOI: 10.1016/J.MPDHP.2020.08.004 [retrieved on Sep. 10, 2020] p. 514-p. 516.

*Primary Examiner* — Atiba O Fitzpatrick
(74) *Attorney, Agent, or Firm* — Bookoff McAndrews, PLLC

(57) ABSTRACT

A computer-implemented method of using a machine learning model to categorize a sample in digital pathology may include receiving one or more cases, each associated with digital images of a pathology specimen; identifying, using the machine learning model, a case as ready to view; receiving a selection of the case, the case comprising a plurality of parts; determining, using the machine learning model, whether the plurality of parts are suspicious or non-suspicious; receiving a selection of a part of the plurality of parts; determining whether a plurality of slides associated with the part are suspicious or non-suspicious; determining, using the machine learning model, a collection of suspicious slides, of the plurality of slides, the machine learning model having been trained by processing a plurality of training images; and annotating the collection of suspicious slides and/or generating a report based on the collection of suspicious slides.

20 Claims, 17 Drawing Sheets

AI USER WORKFLOW (CLINICAL)
200

(51) Int. Cl.
*G06V 10/25* (2022.01)
*G06V 10/12* (2022.01)
*G06V 10/77* (2022.01)
*G16H 10/40* (2018.01)
*G16H 15/00* (2018.01)
*G16H 50/20* (2018.01)
*G16H 30/40* (2018.01)
*G16H 80/00* (2018.01)
*G06T 11/60* (2006.01)

(52) U.S. Cl.
CPC ......... *G06V 10/7715* (2022.01); *G16H 10/40* (2018.01); *G16H 15/00* (2018.01); *G16H 30/40* (2018.01); *G16H 50/20* (2018.01); *G16H 80/00* (2018.01); *G06T 2207/10004* (2013.01); *G06T 2207/30004* (2013.01); *G06T 2207/30024* (2013.01); *G06V 2201/03* (2022.01)

(56) References Cited

U.S. PATENT DOCUMENTS

| 2020/0272864 A1* | 8/2020 | Faust | G06N 3/0454 |
| 2020/0294231 A1* | 9/2020 | Tosun | G06K 9/628 |
| 2020/0372638 A1* | 11/2020 | Gregson | G16H 50/70 |
| 2022/0005582 A1* | 1/2022 | Linhart | G16H 50/30 |
| 2022/0051771 A1* | 2/2022 | Lyman | G16H 30/40 |

FOREIGN PATENT DOCUMENTS

| WO | 2013049153 A2 | 4/2013 | |
| WO | WO-2020075172 A1 * | 4/2020 | ............... G06T 3/40 |
| WO | WO-2020132363 A1 * | 6/2020 | ........... C12Q 1/6886 |

* cited by examiner

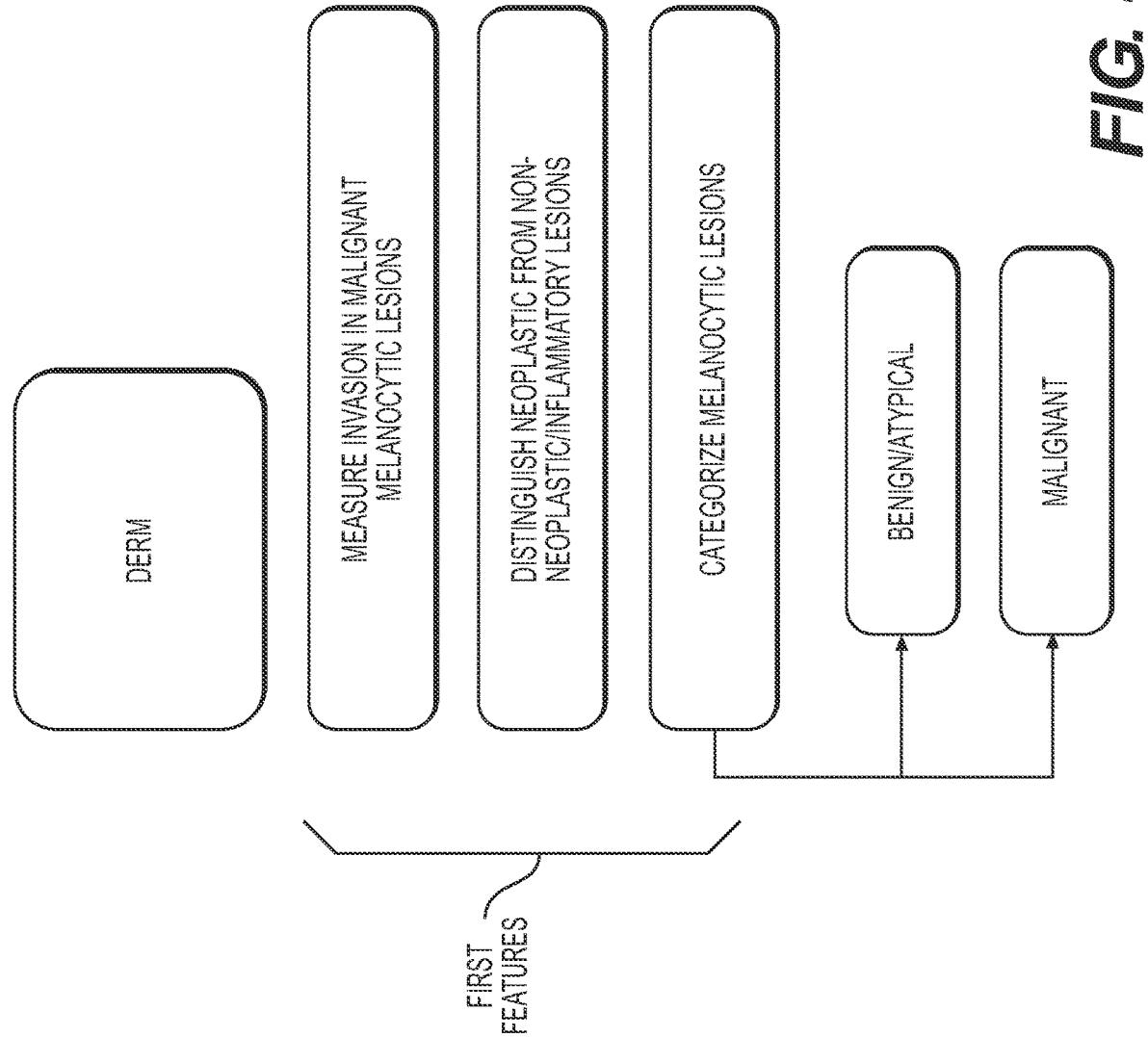

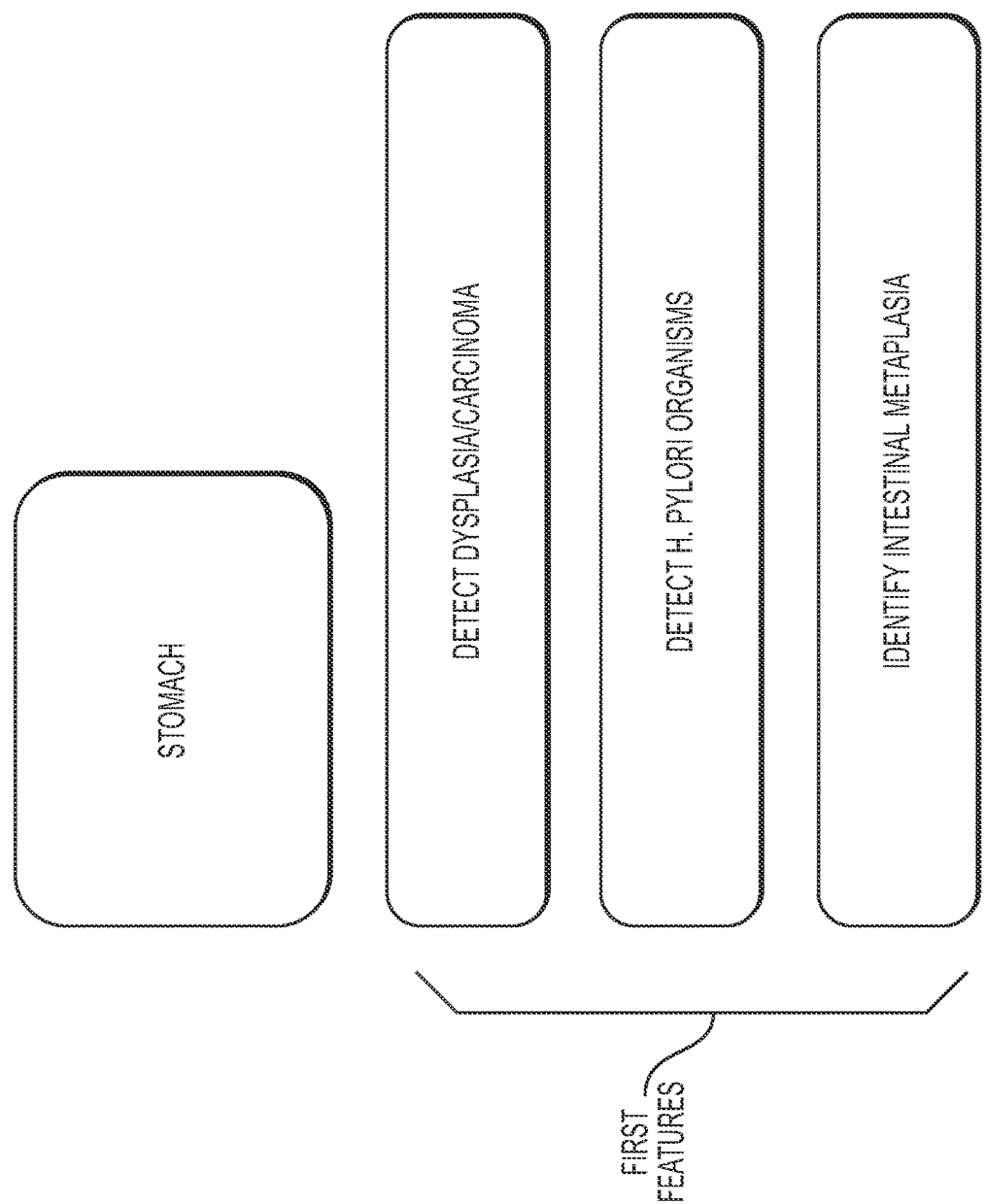

REPORTABLE FEATURES

| FEATURE | REPORTABLE CHARACTERISTICS | | RESECTION ONLY |
|---|---|---|---|
| INVASIVE CANCER | | | |
| IDC | GRADE WELL/MODERATE/POOR (3-5/6-7/8-9) | LENGTH | MARGINS |
| ILC | | | |
| MICROINVASION | | | |
| IN SITU CANCER | EACH AREA OF DCIS EVALUATED FOR: | COMEDONECROSIS: 1) NOT IDENTIFIED, 2) IDENTIFIED, FOCAL, 3) IDENTIFIED, CENTRAL → (ARCHITECTURE) | SINGLE FOCUS, MULTIPLE (PROVIDE ESTIMATE), NUMEROUS (TOO NUMEROUS TO QUANTIFY) |
| DCIS | GRADE: LOW/INTERMEDIATE/HIGH | | MARGINS |
| LCIS | LCIS SUBTYPE: CLASSICAL VS PLEOMORPHIC | | NUMBER OF SLIDES WITH DCIS |
| ATYPIA | | | |
| ADH | PRESENCE | | |
| ALH | PRESENCE | | |
| NON-ATYPICAL HIGH RISK LESIONS | | | |
| RADIAL SCARS, COMPLEX SCLEROSING LESIONS, PAPILLOMAS, ... | PRESENCE | | |
| OTHER | | | |
| CALCIFICATION | | | PRESENCE WITHIN IDC, WITHIN DCIS |
| LYMPHOVASCULAR INVASION (BINARY) | | | |
| PERINEURAL INVASION (BINARY) | | | |

FIG. 7

SYSTEMS AND METHODS FOR PROCESSING ELECTRONIC IMAGES OF SLIDES FOR A DIGITAL PATHOLOGY WORKFLOW

RELATED APPLICATION(S)

This application claims priority to U.S. Provisional Application No. 63/127,846 filed Dec. 18, 2020, the entire disclosure of which is hereby incorporated herein by reference in its entirety.

FIELD OF THE DISCLOSURE

Various embodiments of the present disclosure pertain generally to image processing methods. More specifically, particular embodiments of the present disclosure relate to systems and methods for categorizing artificial intelligence (AI) visualization attributes to create a reusable and scalable framework for unique, AI-enabled visualizations and interactions, resulting in a useful AI-powered digital workflow for pathologists rendering a diagnosis.

BACKGROUND

There are a wide range of tissue and surgical specimen types that may require pathological review and diagnosis. An example of reportable features and instances that may need to be seen, reviewed, and diagnosed by the pathologist may include features and instances within areas such as the bladder, colon, lung, dermatology, and stomach. It may be useful to provide a visualization of a number of areas (e.g., features of bladder, colon, lung, dermatology, and stomach) for a pathologist.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for processing electronic images of slides for a digital pathology workflow.

A computer-implemented method of using a machine learning model to categorize a sample in digital pathology may comprise receiving one or more cases, each associated with digital images of a pathology specimen, at a digital storage device, identifying, using the machine learning model, a case of the one or more cases as ready to view, receiving a selection of the case, the case comprising a plurality of parts, determining, using the machine learning model, whether the plurality of parts are suspicious or non-suspicious, receiving a selection of a part of the plurality of parts, determining whether a plurality of slides associated with the part are suspicious or non-suspicious, determining, using the machine learning model, a collection of suspicious slides, of the plurality of slides, the machine learning model having been trained by processing a plurality of training images, and annotating the collection of suspicious slides and/or generating a report based on the collection of suspicious slides.

Identifying a case as ready to view may include verifying that all slides within the case are processed and uploaded to a digital storage device. Annotating the collection of suspicious slides, in techniques presented herein, may further include outlining at least one region around suspicious tissue (or, alternatively or in addition thereto, nonsuspicious tissue), measuring a length and/or an area of the suspicious tissue (or nonsuspicious tissue), and outputting an annotation onto the collection of suspicious slides.

The method may further include populating the report with information about the collection of suspicious slides (and/or nonsuspicious slides), and outputting the report to a user. Information about the collection of suspicious slides may include a focus area, a contextual area, one or more measurements of suspicious tissue, an alphanumeric output, and/or a compiled report based on all of the focus areas, contextual areas, and/or measurements. The alphanumeric output may include a binary indication of a presence of one or more biomarkers within the tissue. The report and/or visualization of a suspicious tissue may include a detection panel, a quantification panel, and/or an annotation log. The annotation log may be searchable at a case level, at a part level, and/or at a slide level.

The method may further include determining a complexity associated with each of the one or more cases and prioritizing the one or more cases based on the determined complexity. The method may further include sorting and/or filtering for display, using the machine learning model, the plurality of parts based on the determination of whether the plurality of parts are suspicious or non-suspicious. The method may further include determining a pathology type and generating the report based on the determined pathology type.

The method may further include determining, using the machine learning model, a plurality of features based on the digital images associated with the case, determining, using the machine learning model, a plurality of partial reports using the plurality of features, and determining the report based on the plurality of partial reports.

A system for using a machine learning model to categorize a sample in digital pathology may comprise at least one memory storing instructions and at least one processor configured to execute the instructions to perform operations. The operations may include receiving one or more cases, each associated with digital images of a pathology specimen, at a digital storage device, identifying, using the machine learning model, a case of the one or more cases as ready to view, receiving a selection of the case, the case comprising a plurality of parts, determining, using the machine learning model, whether the plurality of parts are suspicious or non-suspicious, receiving a selection of a part of the plurality of parts, determining whether a plurality of slides associated with the part are suspicious or non-suspicious, determining, using the machine learning model, a collection of suspicious slides, of the plurality of slides, the machine learning model having been trained by processing a plurality of training images, and annotating the collection of suspicious slides and/or generating a report based on the collection of suspicious slides.

Identifying a case as ready to view may include verifying that all slides within the case are processed and uploaded to a digital storage device. Annotating the collection of suspicious slides may further include outlining at least one region around suspicious tissue, measuring a length and/or an area of the suspicious tissue, and outputting an annotation onto the collection of suspicious slides. The operations may further include populating the report with information about the collection of suspicious slides and outputting the report to a user. Information about the collection of suspicious slides may include a focus area, a contextual area, one or more measurements of the suspicious tissue, and/or an alphanumeric output.

The operations may further comprise determining a complexity associated with each of the one or more cases and prioritizing the one or more cases based on the determined complexity. The operations may further comprise determining, using the machine learning model, a plurality of features based on the digital images associated with the case, determining, using the machine learning model, a plurality of partial reports using the plurality of features, and determining the report based on the plurality of partial reports.

A non-transitory computer-readable medium may store instructions that, when executed by a processor, perform a method of using a machine learning model to output a task-specific prediction. The method may include receiving one or more cases, each associated with digital images of a pathology specimen, at a digital storage device, identifying, using the machine learning model, a case of the one or more cases as ready to view, receiving a selection of the case, the case comprising a plurality of parts, determining, using the machine learning model, whether the plurality of parts are suspicious or non-suspicious, receiving a selection of a part of the plurality of parts, determining whether a plurality of slides associated with the part are suspicious or non-suspicious, determining, using the machine learning model, a collection of suspicious slides, of the plurality of slides, the machine learning model having been trained by processing a plurality of training images, and annotating the collection of suspicious slides and/or generating a report based on the collection of suspicious slides.

Annotating the collection of suspicious slides may further include outlining at least one region around suspicious tissue, measuring a length and/or an area of the suspicious tissue, and outputting an annotation onto the collection of suspicious slides.

It is to be understood that both the foregoing description and the following detailed description are exemplary and explanatory only, and are not restrictive of the disclosed embodiments.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 4A-4E illustrate example reports for a variety of reportable features and instances that may need to be seen, reviewed, and diagnosed by a pathologist, according to exemplary embodiments of the present disclosure.

FIG. 7 illustrates an exemplary diagram of reportable features, according to exemplary embodiments of the present disclosure.

DESCRIPTION OF THE EMBODIMENTS

Figure 1A:
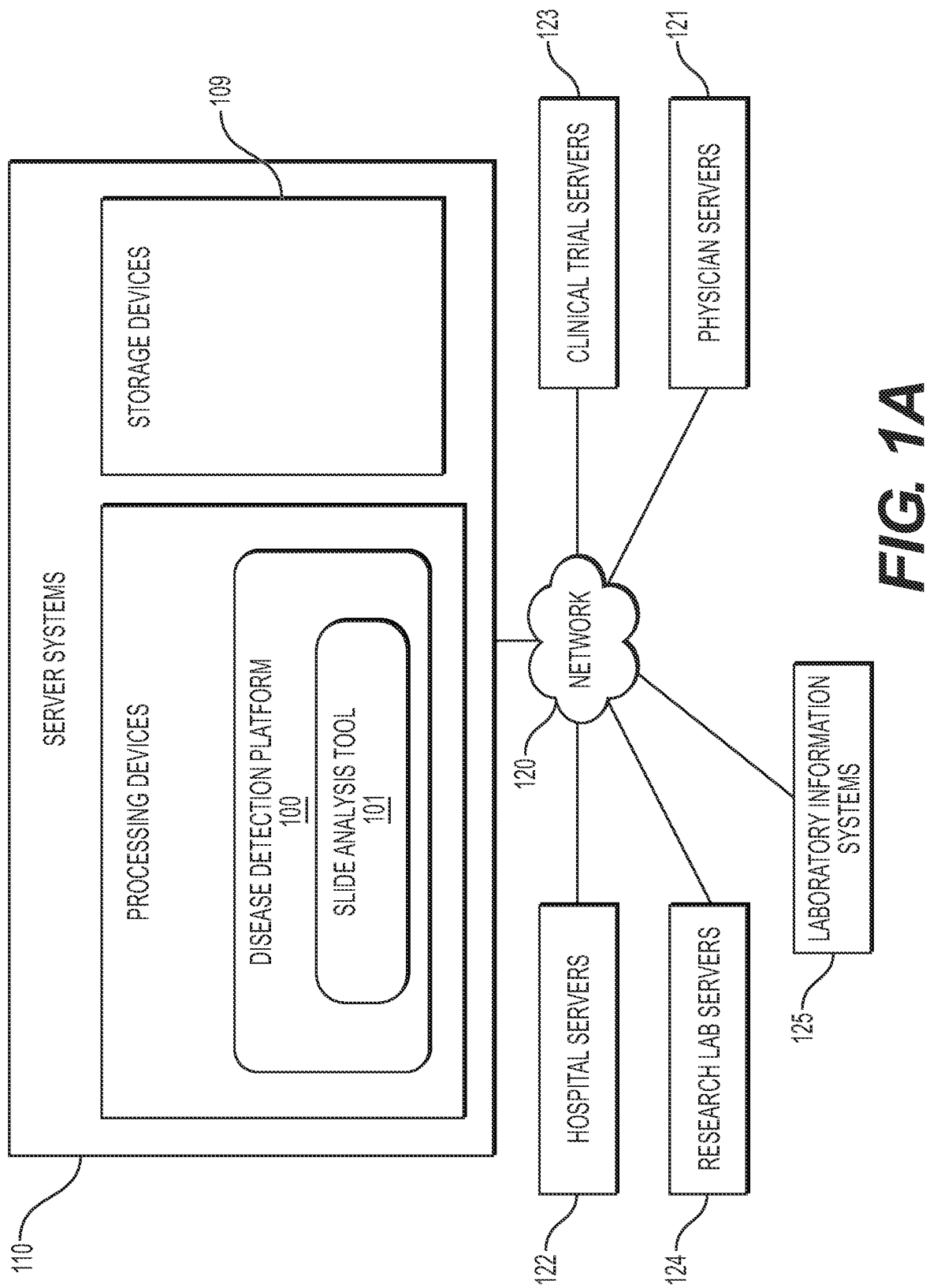
FIG. 1A illustrates an exemplary block diagram of a system and network for categorizing artificial intelligence (AI) visualization attributes to create a framework for an AI-powered digital workflow, according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

FIG. 1A illustrates an exemplary block diagram of a system and network for categorizing artificial intelligence (AI) visualization attributes to create a framework for an AI-powered digital workflow, according to an exemplary embodiment of the present disclosure.

Specifically, FIG. 1A illustrates an electronic network 120 that may be connected to servers at hospitals, laboratories, and/or doctor's offices, etc. For example, physician servers 121, hospital servers 122, clinical trial servers 123, research lab servers 124, and/or laboratory information systems 125, etc., may each be connected to an electronic network 120, such as the Internet, through one or more computers, servers and/or handheld mobile devices. According to an exemplary embodiment of the present application, the electronic network 120 may also be connected to server systems 110, which may include processing devices that are configured to implement a disease detection platform 100, which includes a slide analysis tool 101 for determining specimen property or image property information pertaining to digital pathology image(s), and using machine learning to determine whether a disease or infectious agent is present, according to an exemplary embodiment of the present disclosure. The slide analysis tool 101 may allow for rapid evaluation of 'adequacy' in liquid-based tumor preparations; facilitate the diagnosis of liquid based tumor preparations (cytology, hematology/hematopathology); and predict molecular findings most likely to be found in various tumors detected by liquid-based preparations.

The physician servers 121, hospital servers 122, clinical trial servers 123, research lab servers 124 and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124 and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124 and/or laboratory information systems 125 may transmit digitized slide images and/or patient-specific information to server systems 110 over the electronic network 120. Server system(s) 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the storage devices 109. Server systems 110 may further include one or more machine learning tool(s) or capabilities. For example, the processing devices may include a machine learning tool for a disease detection platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124 and/or laboratory information systems 125 refer to systems used by pathologists for reviewing the images of the slides. In hospital settings, tissue type information may be stored in a laboratory information system 125.

Figure 1B:
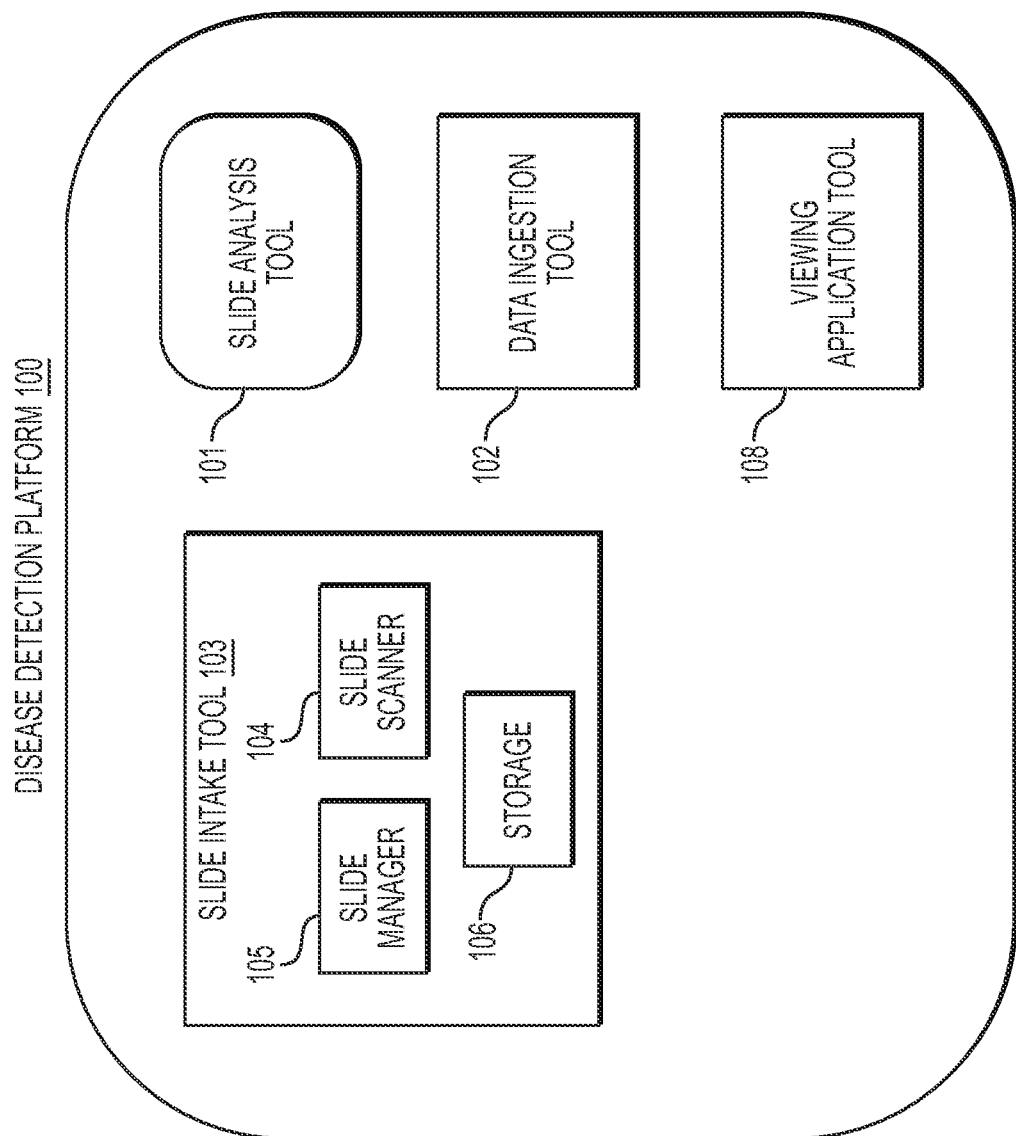
FIG. 1B illustrates an exemplary block diagram of a disease detection platform, according to an exemplary embodiment of the present disclosure.

FIG. 1B illustrates an exemplary block diagram of a disease detection platform 100 for determining specimen property or image property information pertaining to digital pathology image(s), using machine learning. The disease detection platform 100 may include a slide analysis tool 101, a data ingestion tool 102, a slide intake tool 103, a slide scanner 104, a slide manager 105, a storage 106, a laboratory information system (e.g., laboratory information system 125), and a viewing application tool 108.

The slide analysis tool 101, as described below, refers to a process and system for determining data variable property or health variable property information pertaining to digital pathology image(s). Machine learning may be used to classify an image, according to an exemplary embodiment. The slide analysis tool 101 may also predict future relationships, as described in the embodiments below.

The data ingestion tool 102 may facilitate a transfer of the digital pathology images to the various tools, modules, components, and devices that are used for classifying and processing the digital pathology images, according to an exemplary embodiment.

The slide intake tool 103 may scan pathology images and convert them into a digital form, according to an exemplary embodiment. The slides may be scanned with slide scanner 104, and the slide manager 105 may process the images on the slides into digitized pathology images and store the digitized images in storage 106.

The viewing application tool 108 may provide a user with a specimen property or image property information pertaining to digital pathology image(s), according to an exemplary embodiment. The information may be provided through various output interfaces (e.g., a screen, a monitor, a storage device and/or a web browser, etc.).

The slide analysis tool 101, and one or more of its components, may transmit and/or receive digitized slide images and/or patient information to server systems 110, physician servers 121, hospital servers 122, clinical trial servers 123, research lab servers 124, and/or laboratory information systems 125 over a network 120. Further, server systems 110 may include storage devices for storing images and data received from at least one of the slide analysis tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively, or in addition, the present disclosure (or portions of the system and methods of the present disclosure) may be performed on a local processing device (e.g., a laptop).

Any of the above devices, tools and modules may be located on a device that may be connected to an electronic network such as the Internet or a cloud service provider, through one or more computers, servers and/or handheld mobile devices.

Figure 1C:
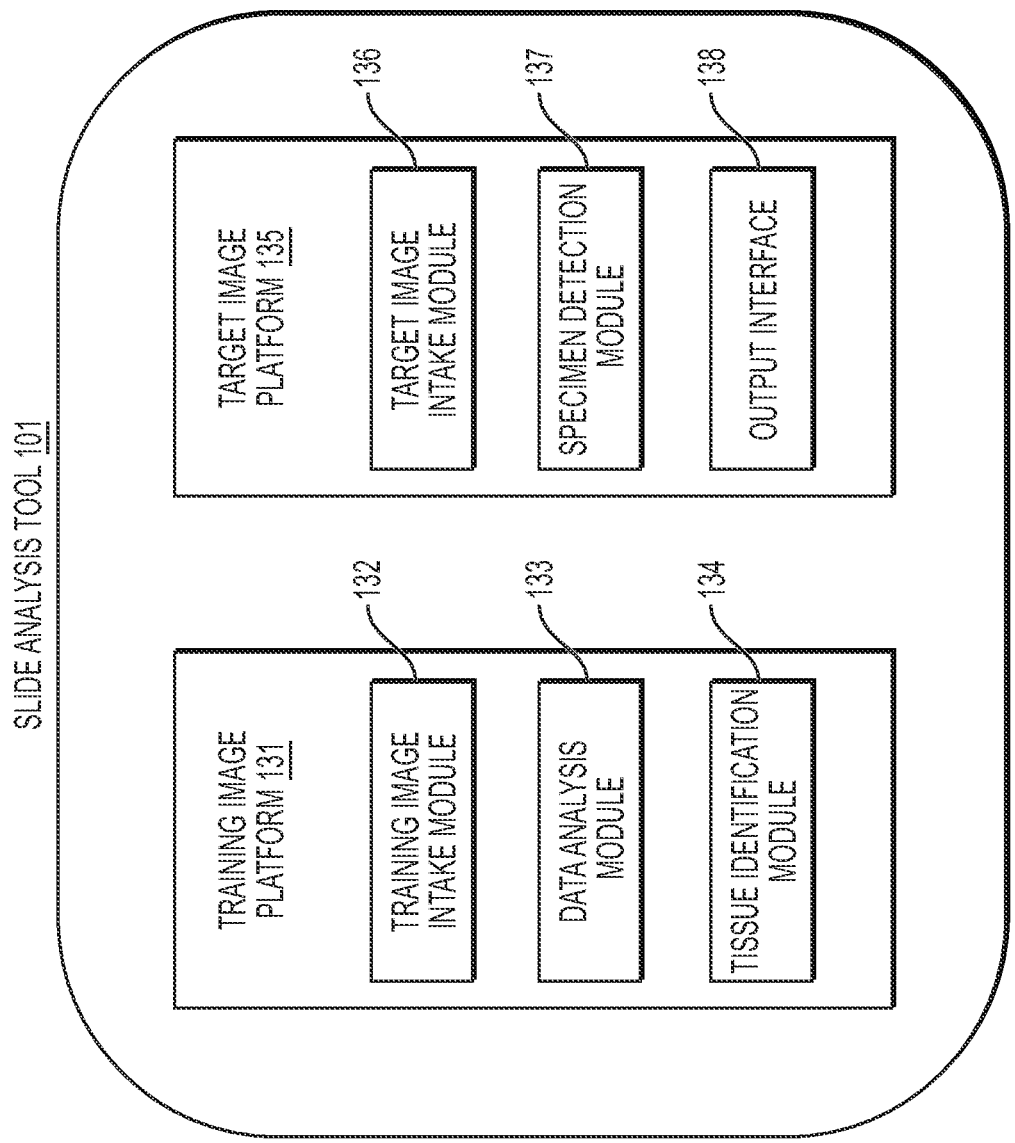
FIG. 1C illustrates an exemplary block diagram of a slide analysis tool, according to an exemplary embodiment of the present disclosure.

FIG. 1C illustrates an exemplary block diagram of a slide analysis tool 101, according to an exemplary embodiment of the present disclosure. The slide analysis tool 101 may include a training image platform 131 and/or a target image platform 135.

According to one embodiment, the training image platform 131 may include a training image intake module 132, a data analysis module 133, and a tissue identification module 134.

The training data platform 131, according to one embodiment, may create or receive training images that are used to train a machine learning model to effectively analyze and classify digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized tissue samples from a 3D imaging device, such as microCT.

The training image intake module 132 may create or receive a dataset comprising one or more training datasets corresponding to one or more specimen tissues. For example, the training datasets may be received from any one or any combination of the server systems 110, physician servers 121, hospital servers 122, clinical trial servers 123, research lab servers 124, and/or laboratory information systems 125. This dataset may be kept on a digital storage device. The data analysis module 133 may identify whether a set of individual cells belong to a cell of interest or a background of a digitized image. The tissue identification module 134 may analyze digitized images and determine whether an individual cell in the cytology sample needs further analysis. It is useful to identify whether an individual cell needs further analysis and to aggregate these areas, and the identification of such may trigger an alert to a user.

According to one embodiment, the target image platform 135 may include a target image intake module 136, a specimen detection module 137, and an output interface 138. The target image platform 135 may receive a target image and apply the machine learning model to the received target image to determine a characteristic of a target data set. For example, the target data may be received from any one or any combination of the server systems 110, physician servers 121, hospital servers 122, clinical trial servers 123, research lab servers 124, and/or laboratory information systems 125. The target image intake module 136 may receive a target dataset corresponding to a target tissue specimen. Specimen detection module 137 may apply the machine learning model to the target dataset to determine a characteristic of the tissue specimen. For example, the specimen detection module 137 may detect a suspicious (and/or non-suspicious) tissue region in the tissue specimen. The specimen detection module 137 may use an artificial intelligence (AI) system that has been trained to identify a presence and/or absence of various features. The AI system may output a map (e.g., tissue map) highlighting all areas related to the identified features or instances of the feature. U.S. application Ser. No. 17/313,617 is hereby incorporated by reference in its entirety. The specimen detection module 137 may determine whether identified features are suspicious or non-suspicious based on certain characteristics such as size, shape, location, proximity to other identified features, disease type, color, stain type, biomarker type, genetic signature, protein type, blood markers, tissue type, tissue texture, calcification presence or level, inflammation presence or level, etc.

The specimen detection module 137 may also apply the machine learning model to the target dataset to determine a quality score for the target tissue specimen. Further, the specimen detection module 137 may apply the machine learning model to the target images to determine whether a target element is present in a tissue specimen.

The output interface 138 may be used to output information about the target tissue specimen and the tissue region of interest. (e.g., to a screen, monitor, storage device, web browser, etc.).

One or more of the exemplary embodiments described below may provide a set of AI visualization types and a set of interaction types. One or more exemplary embodiment may provide examples sorted by tissue type and assigned a visualization type, and any possibly required interaction type to reportable features extracted from the College of American Pathologists (CAP) synoptic. One or more exemplary embodiments may capture clinical use cases, but may also be applied to biomarker products that may leverage one or more defined outputs.

Part and case level aggregation may be a consideration when looking at a pathologist workflow. Pathologists may report and diagnose a tissue specimen on a part level using a part-level aggregation. However, pathology reports may not include slide level observations. In some cases, reporting fields may not be seen at the slide level. Some reporting fields may only be seen at the part level, such as the number of slides in a part with ductal carcinoma in situ (DCIS), for example.

The below definitions are explanatory only and are not intended to be limiting. Whole slide images (WSIs) may refer to one or more images of tissue, stained or unstained. A reportable feature may refer to a classified or labeled area or focus of suspicious tissue as well as any observation of the tissue that is used in diagnoses. A feature instance may be a cite of a reportable feature defined by diagnostic and anatomic characteristic that may be unique to that reportable feature. A visualization type may refer to a display category of a feature instance. An interaction type may refer to a way in which a user may navigate between two or more feature instances. An instance definition may refer to one or more anatomical features that may be necessary to include in an instance display. An AI system or module may refer to one or more modules implementing AI, machine learning technology, and/or a machine learning algorithm, and may not necessarily be limited to a single module, device, system, platform, etc. Aspects disclosed herein may be used on any type or arrangement of AI or machine learning systems, modules, platforms and/or image analysis and/or process systems. Various outputs may be aggregated. A machine learning model may refer to a model or process implementing machine learning technology (e.g., to recognize patterns), and may not be limited to one model. Aspects disclosed herein may use multiple machine learning models which may be combined and/or yield individual outputs which may be later combined and/or aggregated.

Figure 2:
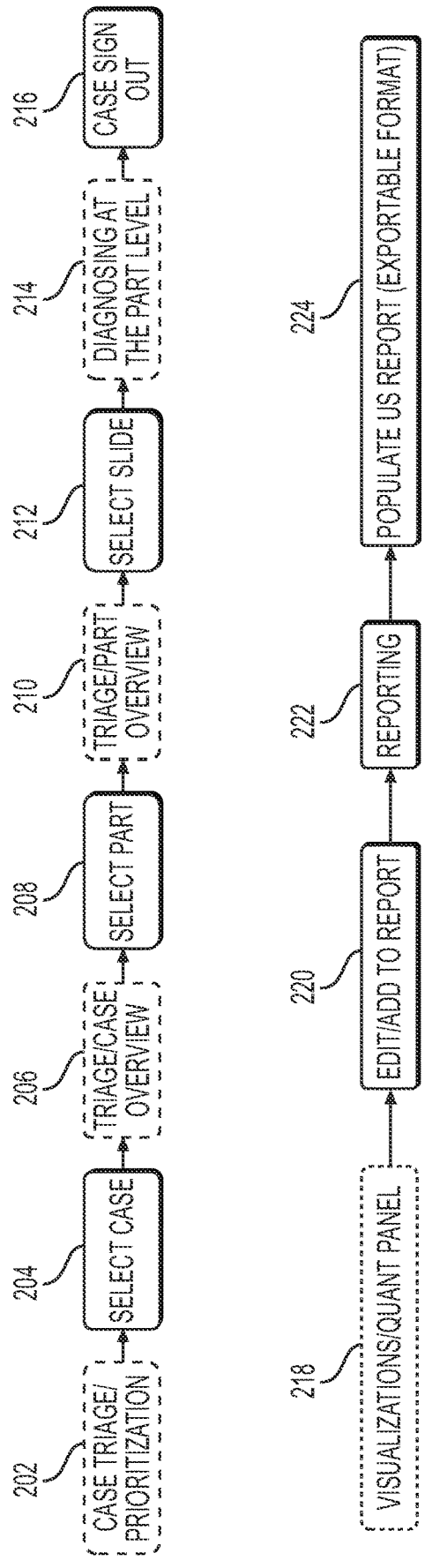
FIG. 2 illustrates an exemplary AI user clinical workflow, according to an exemplary embodiment of the present disclosure.

FIG. 2 illustrates an exemplary AI user workflow 200 in a clinical setting, according to an exemplary embodiment. The exemplary workflow may begin with a step 202, where case triage and/or prioritization may occur (clinical user workflow description). A user may want to be alerted when cases are ready to view, i.e., when all slides associated with a case have been processed and/or uploaded to the system. The user may additionally want to know which cases should be prioritized based upon complexity, for example, and/or by which cases may need an additional order, such as being sent for molecular testing or to be recut.

Complexity may be determined by a diagnosis (e.g. an AI system may classify a slide as Gleason 3+4=7 with relatively low confidence, or may determine a percentage likelihood of Gleason pattern 3 to be 49.9% and a percentage of Gleason pattern 4 may be 50.1%, indicating a borderline case), and/or a need for additional tests beyond an H&E slide to determine a diagnosis (for example, if a condition appears invasive and requires additional stained images for review like estrogen receptor (ER), progesterone receptor (PR), human epidural growth factor receptor 1 (HER2)).

Complexity may be determined based on a combination of AI outputs and known workflows and testing steps required by pathology. Complex cases may be prioritized for earlier in the day and/or may be distributed to more experienced pathologists.

In step 204, the workflow may include the selection of a case, for example from a user.

In step 206, the workflow may include a triage and/or case overview. Similar to step 202, the user may want to see a brief overview of the case or triage information. During and/or before this overview step of 202, the identified features and any other metadata (e.g. user-generated annotations) may be summarized.

In step 208, the workflow may include the selection of a part. The selection may be accompanied by an indicator, which may signal whether the part appears suspicious, non-suspicious, or "other", where "other" may be indicative of a preprogrammed quality or of an unknown variable.

In step 210, the workflow may include a triage and/or part overview step. This overview may include a part index. The user may want to see an overview of what is in the part, but may not need to see slides. By concentrating on the part level, the user may be able to see key areas of focus and/or imagery/visualizations of the key areas.

In step 212, the workflow may include selecting a slide. An associate indicator may be available, which may signal whether the part appears suspicious, non-suspicious, or "other", where "other" may be indicative of a preprogrammed quality or of an unknown variable.

In step 214, the workflow may include diagnosing at the part level. The diagnosis may include a part index with the diagnosis. The AI may aggregate the parts of the pathology specimen to create the part index. As the user may need to make a report at the part level, an aggregated part level index may streamline the user's process for generating a report.

In step 216, the workflow may conclude with a case sign out.

While the clinical workflow is running, the AI may additionally generate a report for the slides examined and resulting diagnosis. In step 218, the workflow may include displaying a visualization and/or quantification panel, based on the results of the part level diagnosis.

In step 220, the visualization and/or quantification panel may be edited and/or added to a report.

In step 222, the workflow may send the report to a user. All reporting may occur at the part level. For each tissue type and between biopsy and resection within a tissue type, reportable features may vary. The type of tissue and procedure may determine what slide level data may be carried to the part level report. For reporting, it may be necessary to aggregate across parts by averaging out varying data from across the slide. Additionally, the presence or absence of a feature may be reported. There may be some features of reporting not present at the slide level; for example, in breast tissue examination, a pathologist may report how many of the slides in the part have DCIS. Annotations or outputs of the AI workflow may be added to the report, such as relevant screenshots and/or identified regions.

Additionally, in step 224, the report may be used to populate a laboratory information system (LIS) report in an exportable format, such as a PDF, etc.

Table 1 illustrates an example of a slide level visualization framework. The focus of the slide may be described using a rectangular indicator overlay on the slide itself, with a contextual area described using a tissue map or otherwise outlines region. Anatomical elements within the focus may be useful for the effectivity of the display, as well as a set of coordinates and the size and/or zoom level associated with the area of focus. Metadata may accompany the slide level visualization, and may include a name for the focus area (such as "calcification"), metric and/or text output, and size of the focus area.

The contextual area may aggregate any or all instances throughout a slide, as the count of instances may be important for some visualization types. Potential accompanying metadata may include a name for the contextual area (such as "breast subtype"), and a metric and/or text output, which may include a name of the subtype, a size and/or measurement of the contextual area, a grade associated with the contextual area, an architecture of the contextual area, etc.

A measurement of the tissue specimen may be shown on the visualization as a line with clearly labeled endpoints. The measurement may be accompanied by a name (such as "prostate" or "tumor length", for example), as well as a metric and/or text output (such as the numeric measurement of the line).

Text or numeric output may also be included in the slide level visualization, and may be displayed directly on the visualization. The text or numeric output may include metadata, such as a name or other metric and/or text output, associated with the tissue specimen or independent annotations added by the user during review. The metadata may include, for example, a detected biomarker.

A compiled report of the visualization may be included on the slide level visualization, and may be formatted by an external vender. The compiled report may be associated with a WSI or a specific region of interest. The report, for example a PDF report, may include a slide ID and an overall score for the slide, among other relevant information.

TABLE 1

Slide Level Visualization Framework

|  | Focus | Contextual Area | Measurement | Alphanumeric | Compiled report |
|---|---|---|---|---|---|
| Visualization Description | Focus notated with rectangle indicator | Tissue map or otherwise outline region | Line with endpoints | Text or numeric output | Report formatted by external vendor |
| Details of Display | Anatomical elements useful for effectivity of display Coordinate of focus Size/zoom level | May aggregate any or all instances throughout slide |  | Metadata vs independent | Associated with a WSI or region of interest |
| Potential Accompanying Metadata | Name, Metric/text output, Size | Name, Metric/text output | Name, Metric/text output | Name, Metric/text output | Slide ID, Overall score (?) |
| Example | Calcification | Breast subtype (except for DCIS) | Prostate Tumor Length | Detected Biomarker | PDF report |
| Example Metadata |  | Name of subtype, size/measurement, grade, architecture | Numeric measurement |  |  |

Figure 3:
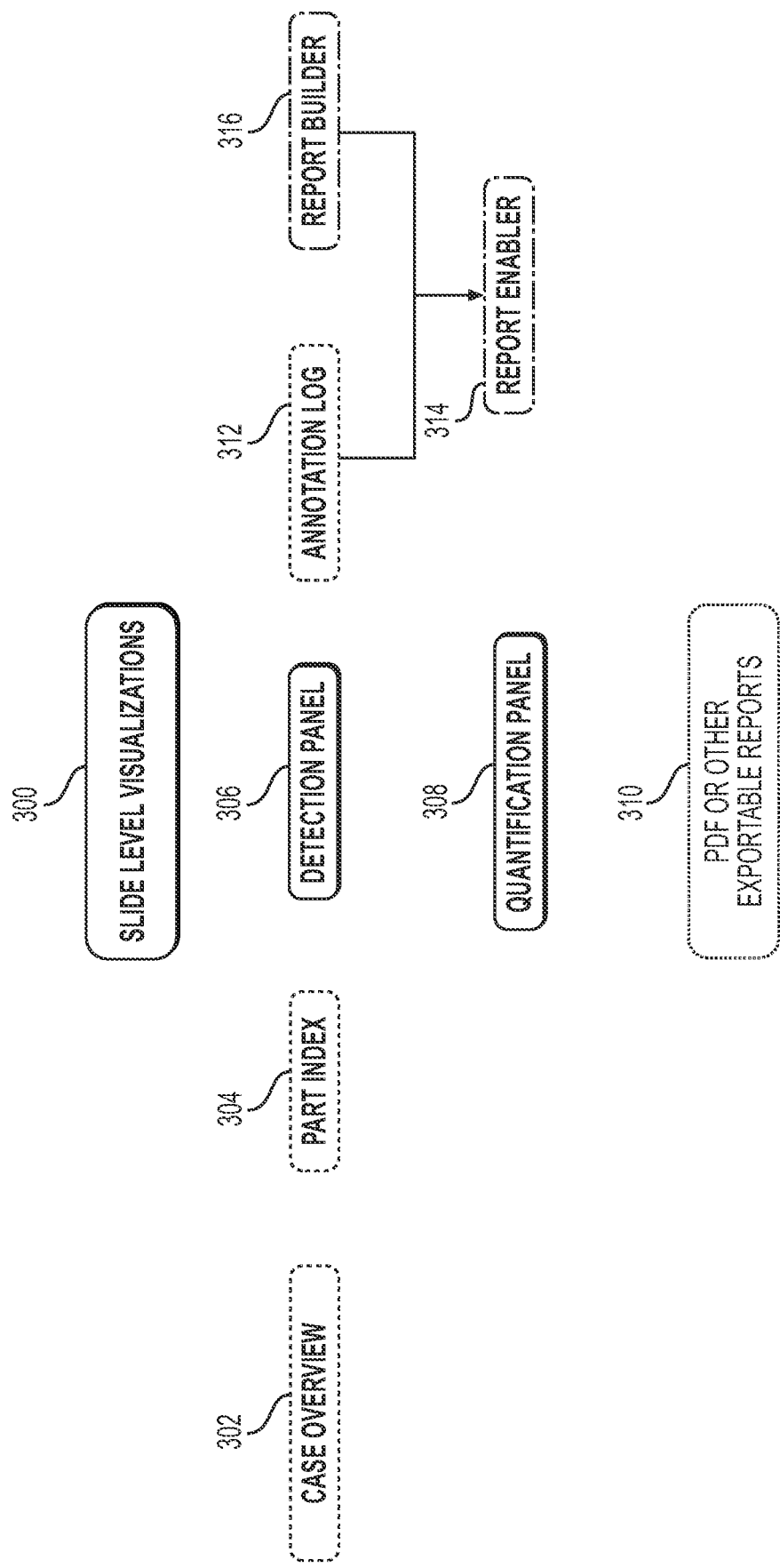
FIG. 3 illustrates an exemplary diagram of slide level visualizations, according to an exemplary embodiment of the present disclosure.

FIG. 3 depicts an exemplary diagram of an overall framework for AI-enabled visualizations. The slide-level visualization 300 may include a case overview 302, a part index 304, a detection panel 306, a quantification panel 308, one or more exportable reports 310. Additionally, the framework may include an annotation log 312 and a report builder 316, which together may form a report enabler.

In the case overview 302, the framework may include an AI-driven case overview and triage information available to a user before the user begins reviewing slides. The case overview may include, for example, an accession identification number or other sort of identifier, a status (e.g., ready, reviewed, not ready), an access date, patient name, a medical record number or MRN, a type of tissue (e.g., breast, dermis or derm, gastrointestinal or GI, or prostate), a specimen type (e.g., biopsy), and a number of slides. Another portion of the case overview may include visualizations, snapshots, or a "slide tray" of the slides, which may include identifiers (e.g., "right breast"), a type of stain (e.g., H&E), and other information.

The part index 304 may include an AI-driven part overview and triage information available to the user before the user begins reviewing slides.

The detection panel 306 may be a templated panel that may enable a binary classification of a tissue as suspicious or non-suspicious.

The quantification panel 308 may include a quantification, a sorting, and/or a filtering of tissue features and/or other reportable features. Quantification, sorting, and/or filtering may be based on determinations of suspicious and non-suspicious and/or other determinations. As an example of quantification, in a prostate case, an amount of tumor may be quantified as a percentage and/or as a distance or area metric in, for example, millimeters (mm). Distinct instances of the feature (e.g., perineural invasion) may also be sorted and/or filtered according to a probability of severity or a likelihood based on an AI system detecting the instance. For example, during filtering, distinct instances having a low (e.g., lower than a threshold) probability of severity may be removed before the sorted and/or filtered features are output. The quantification panel 308 may be joined with the detection panel 306 as one panel.

One or more exportable reports 310 may be output from the quantification panel 308 and the detection panel 306. The exportable reports 310 may be in the form of a PDF.

An annotation log 312 may include an activity log of all user-generated notes associated with a tissue specimen. The annotation log 312 may be searchable at both the case and part levels, and each annotation or user-generated note may include a time stamp, a user name and role, a thumbnail image, and/or one or more additional user comments.

The annotation log 312 may be combined with a report builder 316 to create a report enabler 314. The report builder 316 may be valuable with an AI component, as it may be prefilled. Additionally, the report builder 316 may be editable, and may pull information and annotations from the annotation log 312.

The report enabler 314 may include a part level aggregation of the user-generated annotations and the AI-prefilled report. The part level aggregation and/or the AI-prefilled report may be integrated with a clinical system and logged in a patient medical record. A pathologist may review the part level aggregation and/or AI-prefilled report and add edits or annotations to on-canvas visualizations. As the pathologist makes these edits or annotations, the AI-prefilled report may be automatically updated based on the edits, as reportable feature categories may be associated with synoptic reporting fields. In addition, as the pathologist makes these edits or annotations, other features (e.g., child features) related to an edited feature may be automatically updated or adjusted based on the edits.

There are a wide range of tissue and surgical specimen types that may require pathological review and diagnosis. FIGS. 4A-E illustrate example reports for a variety of reportable features and instances that may need to be seen, reviewed, and diagnosed by a pathologist.

Figure 4A:
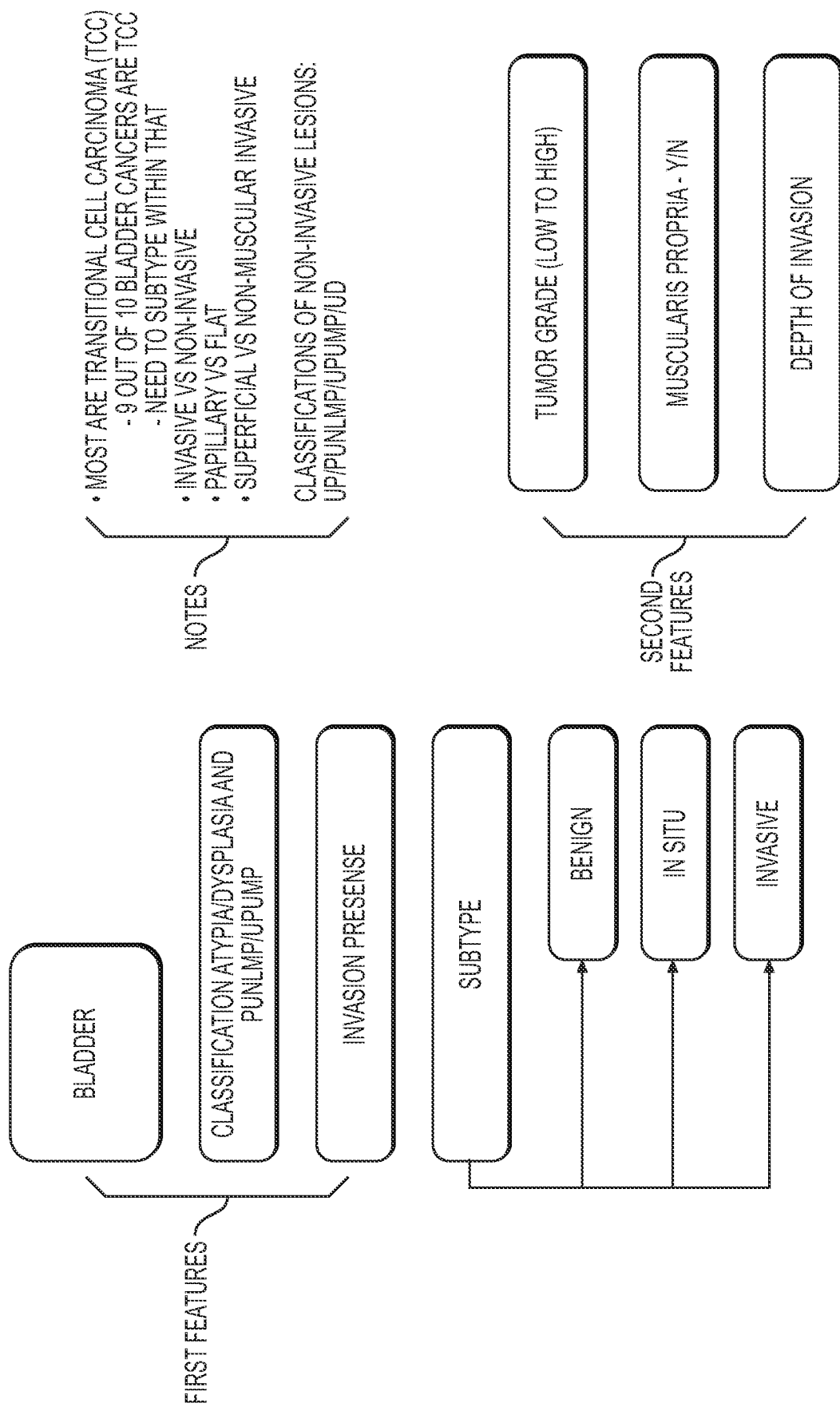

FIG. 4A illustrates an example report for a bladder tissue specimen. At least one first feature is reported; for example, a classification, a presence or an absence of an invasion, and a subtype, including whether the tissue specimen is benign, in situ, invasive, etc. One or more second feature may also be included in the report, such as a tumor grade, a binary indication of muscularis propria, and/or a depth of invasion. User notes may also be included in the example report.

Figure 4B:
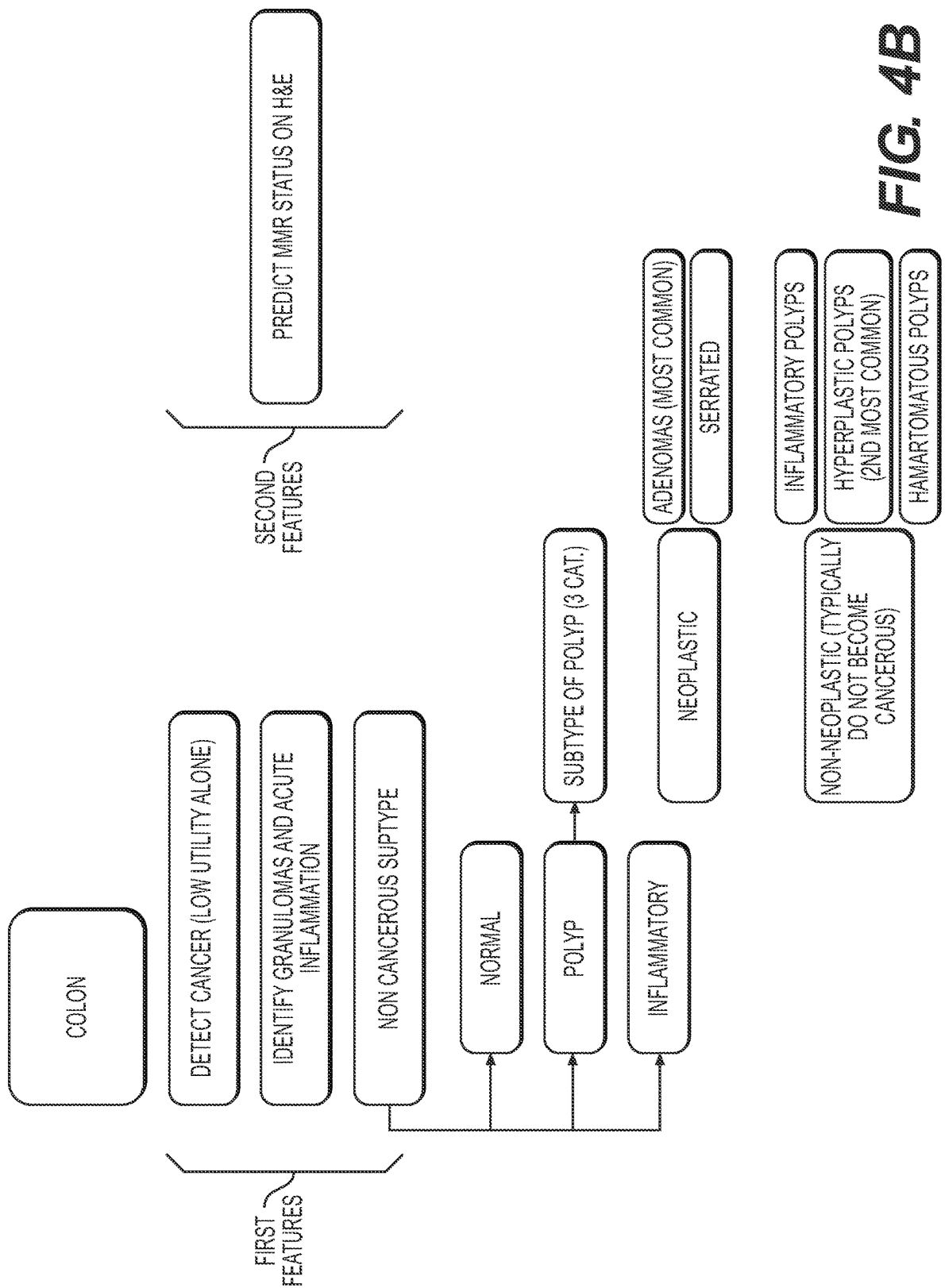

Likewise, FIG. 4B illustrates an example report for a colon tissue specimen, reporting first and second features. The first features may include detecting cancer, identification of granulomas and acute inflammation, and a non-cancerous subtype. The non-cancerous subtype may be further reported as normal, polyp, or inflammatory and additional information, such as subtype polyp, may also be included on the report. A second feature may include a prediction of MMR status on H&E.

Figure 4C:
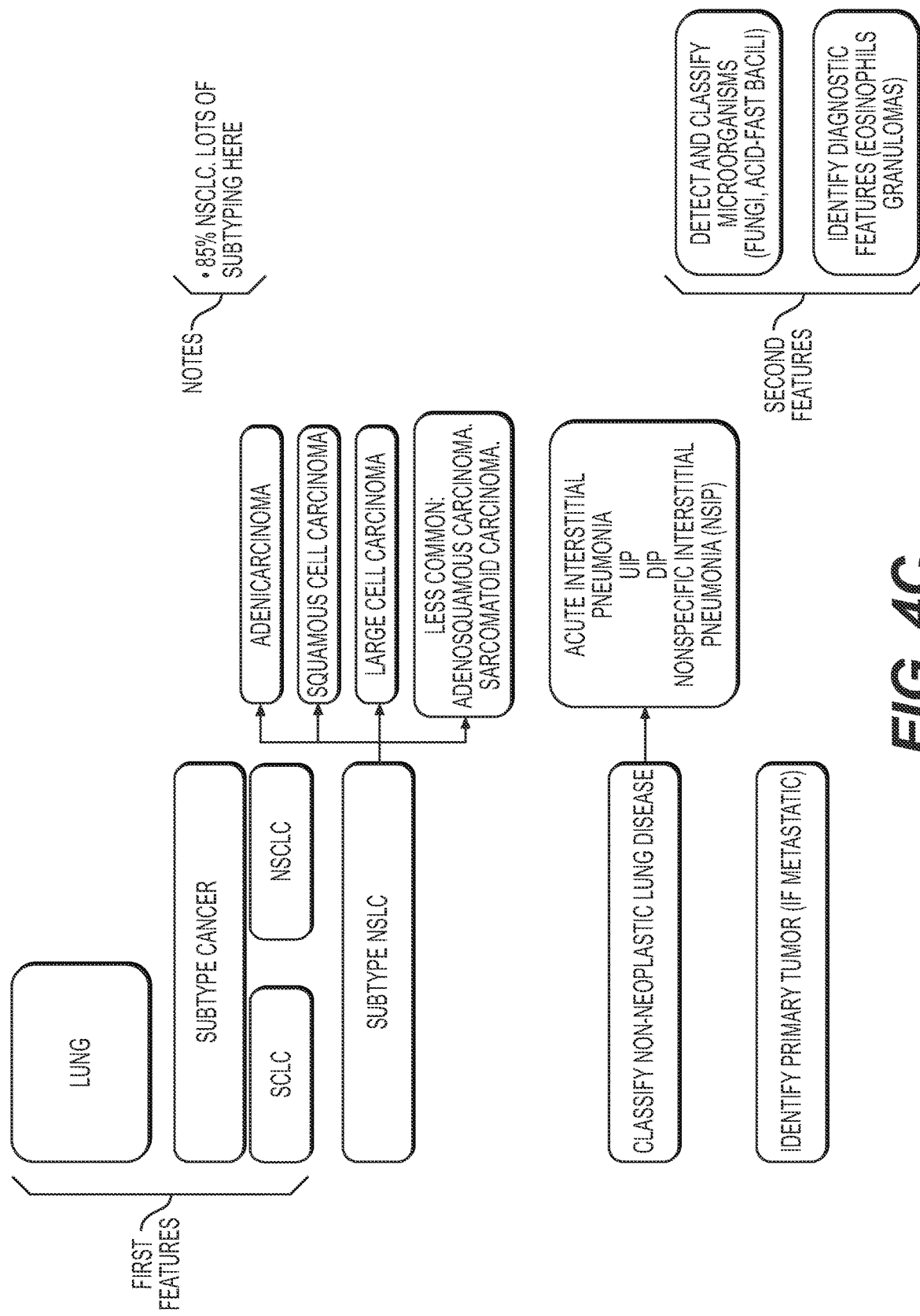

FIGS. 4C, 4D and 4E illustrate example reports for a lung tissue, a dermal tissue, and a stomach tissue, respectively. The exemplary reports may include a variety of reported first and second features, depending on the tissue specimen and a categorization or subtype of the tissue.

Figure 5:
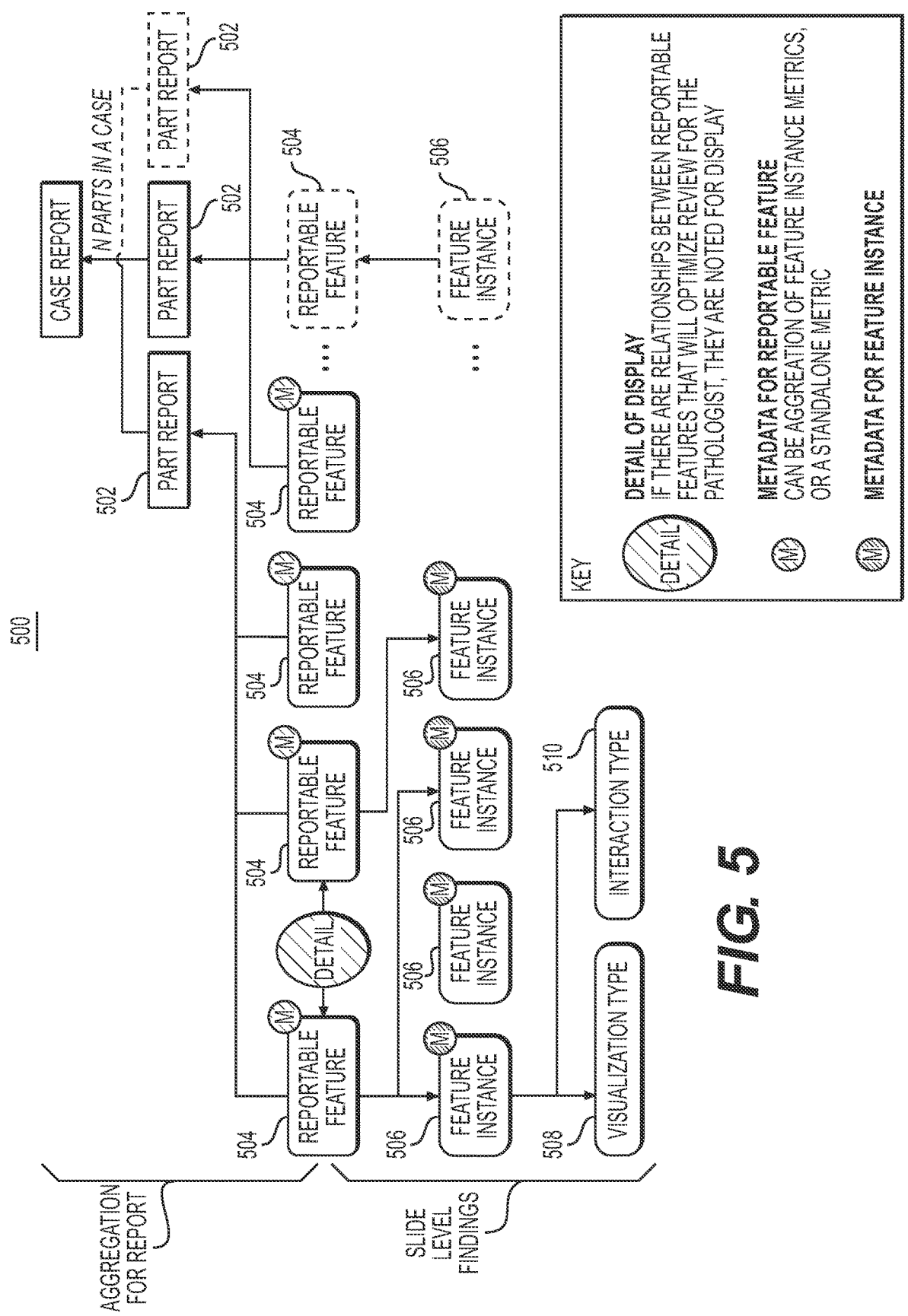
FIG. 5 illustrates an exemplary diagram of an overall framework for an AI-enabled visualization, according to an exemplary embodiment of the present disclosure.

FIG. 5 illustrates an exemplary diagram of an overall framework for an AI-enabled visualization. The overall framework may include two distinct divisions, a number of slide level findings, and an aggregation of the findings by the AI system to create an overall case report.

The case report 500 may include n number of parts in the specific case at hand. Each part may have its own corresponding part report 502. The part report may contain slide level findings, and may include some number of reportable features 504 with associated metadata. If there are relationships between reportable features that may optimize review for the pathologist, they may be noted for display on the visualization. The reportable feature may include one or more feature instances 506 with associate metadata. Each feature instance may include a visualization type 508 and/or an interaction type 510.

A feature instance 506 may be an instance of a reportable feature 504 that is not connected to another reportable feature by tissue. Instances per reportable feature 504 may be defined by diagnosis and anatomy. Feature instances 506 in a slide may be aggregated in a few forms. A user may view some or all instances of a reportable feature 504 in one place (e.g., total tumor and invasive ductal carcinoma (IDC) as tissue map, or all foci of DCIS in gallery view). If a feature instance 506 is associated with metadata, the metadata may be aggregated to create metadata for the reportable feature (e.g. 5 mm of Pattern 3 and 5 mm of Pattern 4 are aggregated for total tumor linear extent (10 mm)).

Table 2 further illustrates associated information regarding feature instances, such as feature instances 506 and instance aggregation. Within a feature instance, a user may "tissue hop" through an instance, or jump between instances on a slide. Instances viewed in the context of the slide as isolated instances may be viewed with a high power setting. A corresponding visualization may be two or more focus areas (if multiple elements are necessary to include an instance) and the surrounding context areas. An example may be an invasion of a disease on a tissue, where multiple feature instances may be necessary to view. A user may also view a feature instance using a gallery view. The gallery may include thumbnails of the feature instances displayed for a quick review, with an option for the user to jump to a specific instance by selecting the thumbnail. A gallery view may correspond to one or more focus areas (although only one focus area may be necessary to include an instance).

In cases of instance aggregation, all areas of a type of tissue may be included in one aggregate group. All instances of that type may be viewed together at a low power. A corresponding visualization type may include context areas.

TABLE 2

| | Feature Instance Tissue Hop | Gallery | Instance Aggregation |
|---|---|---|---|
| Interaction Definition | User can jump between instances across the slide | Thumbnails are displayed for quick review | All areas of that type may be included in one aggregate group |
| | Instances viewed in context of the slide as isolated instances as high power | Instances are viewed as thumbnails with option to jump to instance on click | All instances of that type may be viewed together at low power |
| Corresponding Visualization Type | Foci*, context areas | Foci* | Context areas |
| | *if multiple elements necessary to include in instance | *Only one element may be necessary to include in instance | |
| Example | Invasions-where multiple elements are necessary | Calcification | |

Part (or specimen) level aggregation may be important to the pathology workflow, particular when considering report enablement.

All visualizations may have tissue hop, as described in Table 2. Tissue hop may allow a user to "hop" between any visualization of a tissue type that is found across the part. For example, if one part includes three instances of IDC, though IDC is an aggregate, tissue hop can move the user between those aggregate instances.

The case report 500 may be editable. Apart from any biomarker, all alphanumeric outputs (either metadata or otherwise) may be editable. For example, a measurement end point may be editable, and measurement may be updated during a reporting and/or editing state. Likewise, a future state tissue map area may be editable. A calculated percentage or measured length may update during the reporting and/or editing state. Other metadata might not be recalculated.

The overall framework depicted in FIG. 5 is not limited to particular AI or image analysis and/or processing systems, and aspects disclosed herein may be used for any type of AI or image analysis system. For example, multiple systems and/or modules may be used in the overall framework, and multiple system outputs may be visualized and aggregated for an image, part, case and/or patient.

FIGS. 6A-6D illustrates an exemplary diagram of how common visualizations and interactions for different tissue types may be applied.

Figure 6A:
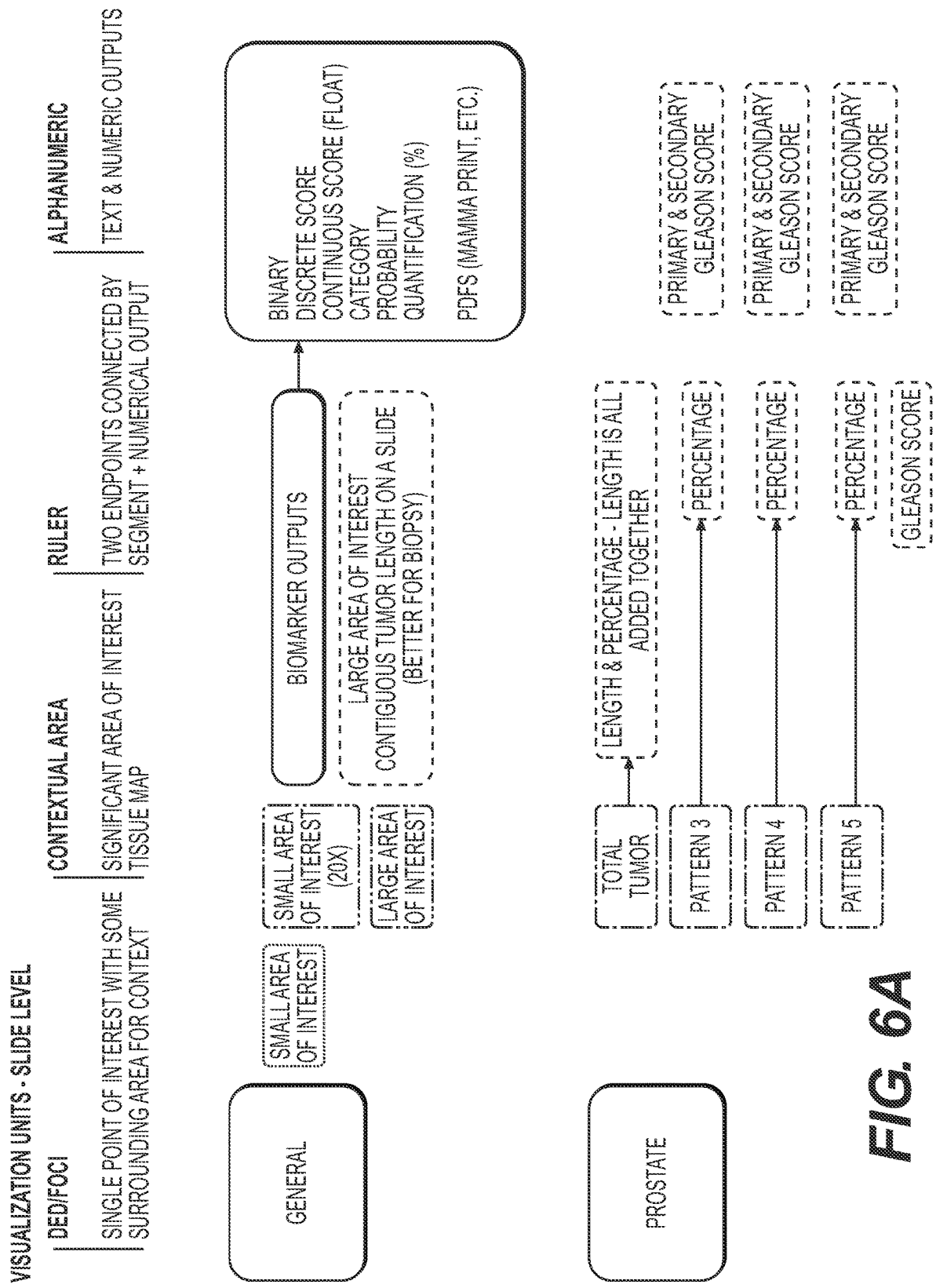
FIGS. 6A-6D illustrates an exemplary diagram of how common visualizations and interactions for different tissue types may be applied, according to an exemplary embodiment of the present disclosure.

FIG. 6A illustrates an example of a general tissue specimen visualization and a prostate tissue specimen visualization. Within the general tissue specimen, a small area of interest is identified as a focus. Alternatively, a small area of interest and a large area of interest may be identified as the foci. The foci may be a single point of interest with some surrounding area of context. The contextual area for a general tissue specimen may include a significant area of interest, and/or a tissue map. This may be shown as a large area of interest, for example, a contiguous tumor length on a slide (which may be better for a tissue biopsy). A ruler tool may be used to measure either a large or small area of interest, with a numerical output. The ruler may be used to measure one or more biomarkers within the specimen tissue. One the slide level visualization, an alphanumeric display may include text and numeric output overlaying the slide. These outputs may be binary, a discrete score, a continuous score, a category, a probability, a quantification (including a percentage), and/or a portable document format (PDF) or other format report output. In a case of a PDF report, the PDF report may be a static report that may not be easily edited. The PDF report may, for example, be associated with a molecular test, CLIA-lab test result, or other test or lab results intended to remain unedited or unmanipulated.

For the prostate tissue specimen example in FIG. 6A, a foci visualization may include a total tumor, as well as one or more patterns. The contextual area may vary depending on the foci in question; for example, a total tumor may include the entire length of the tumor, and the user may measure the length of the tumor, added together if needed. A pattern may be described or measured by a user to include a percentage of tissue covered by the pattern. Additionally, an alphanumeric display may output a primary and/or secondary Gleason score.

Figure 6B:
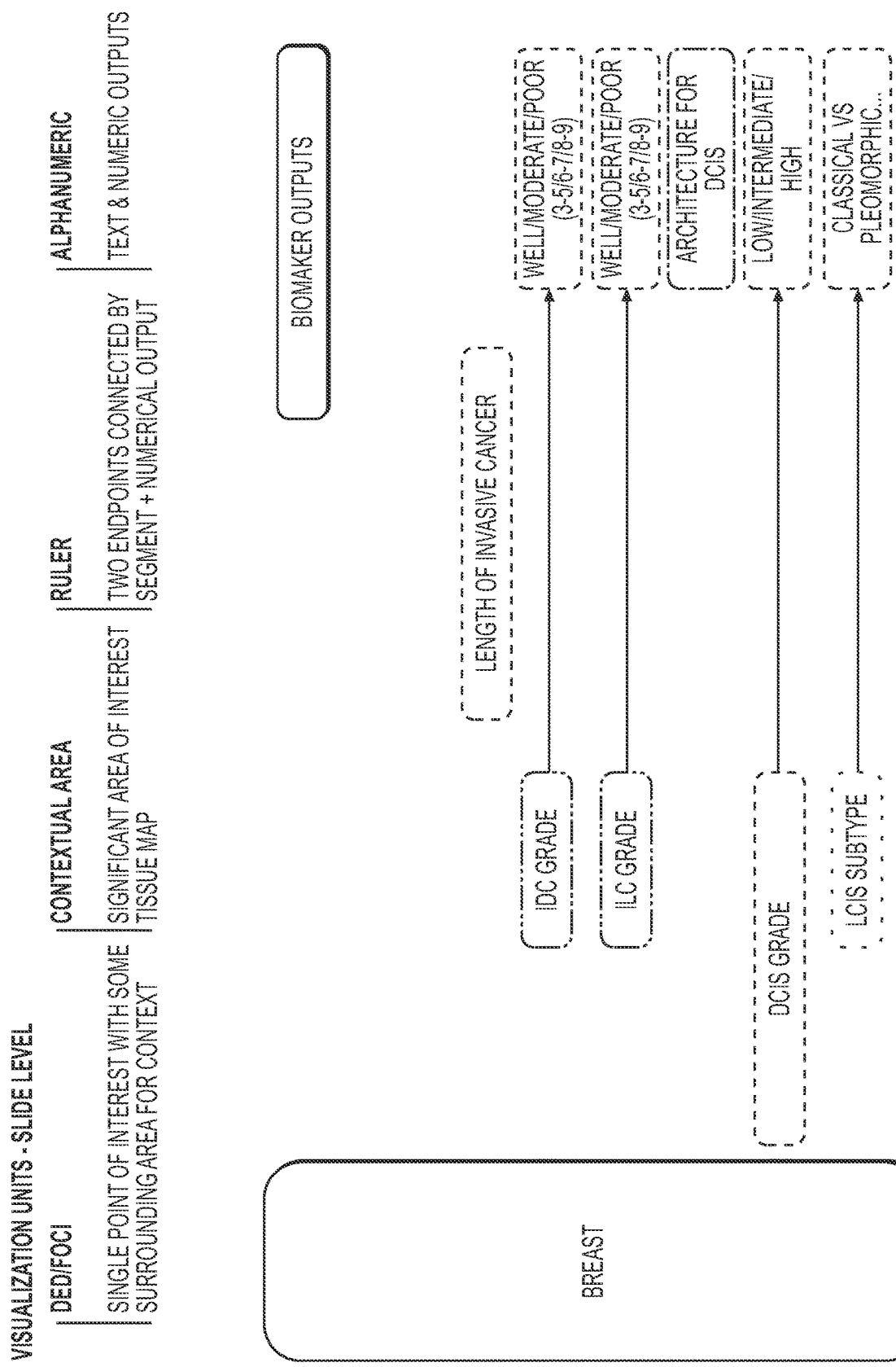
Figure 6C:
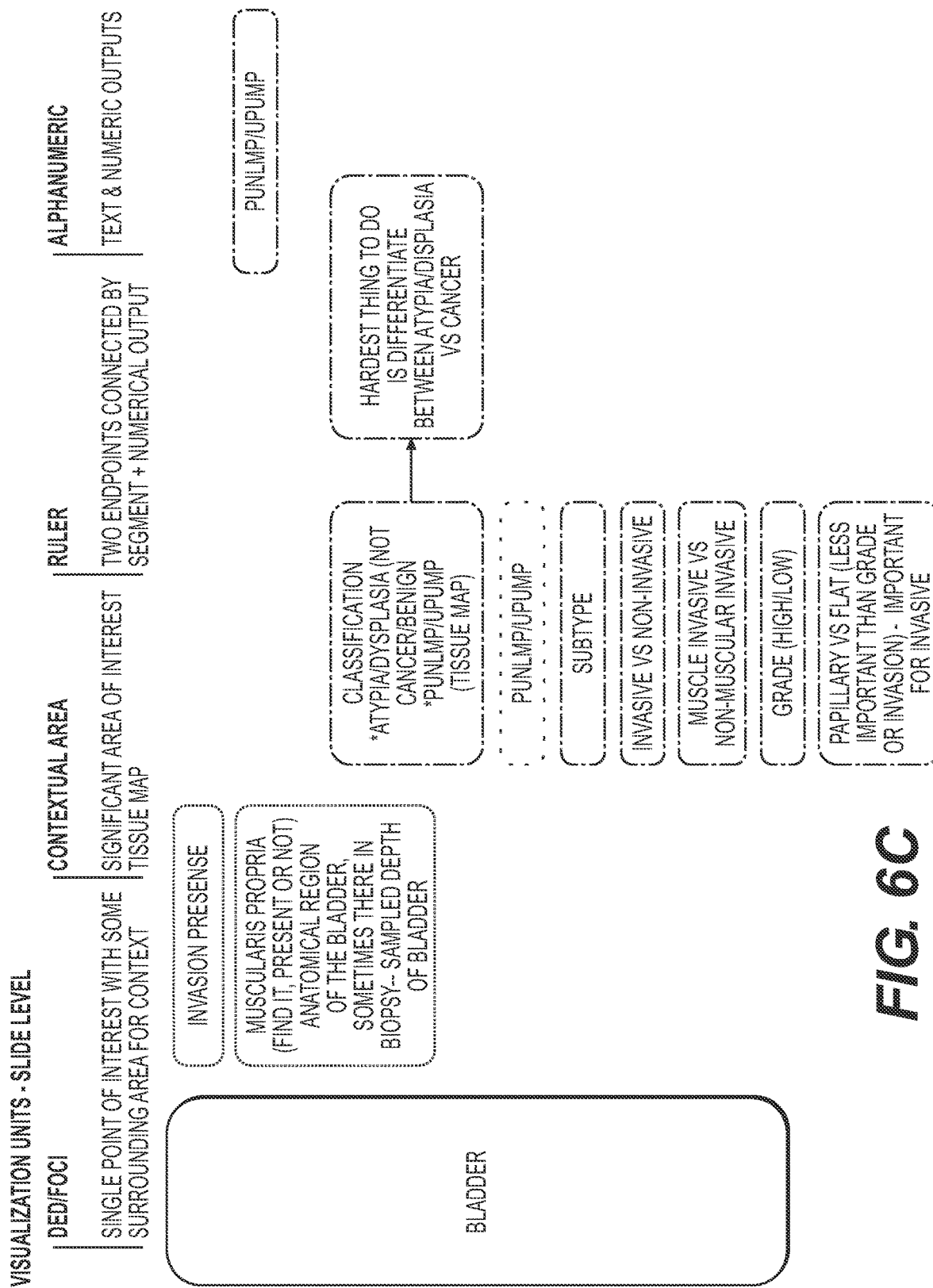
Figure 6D:
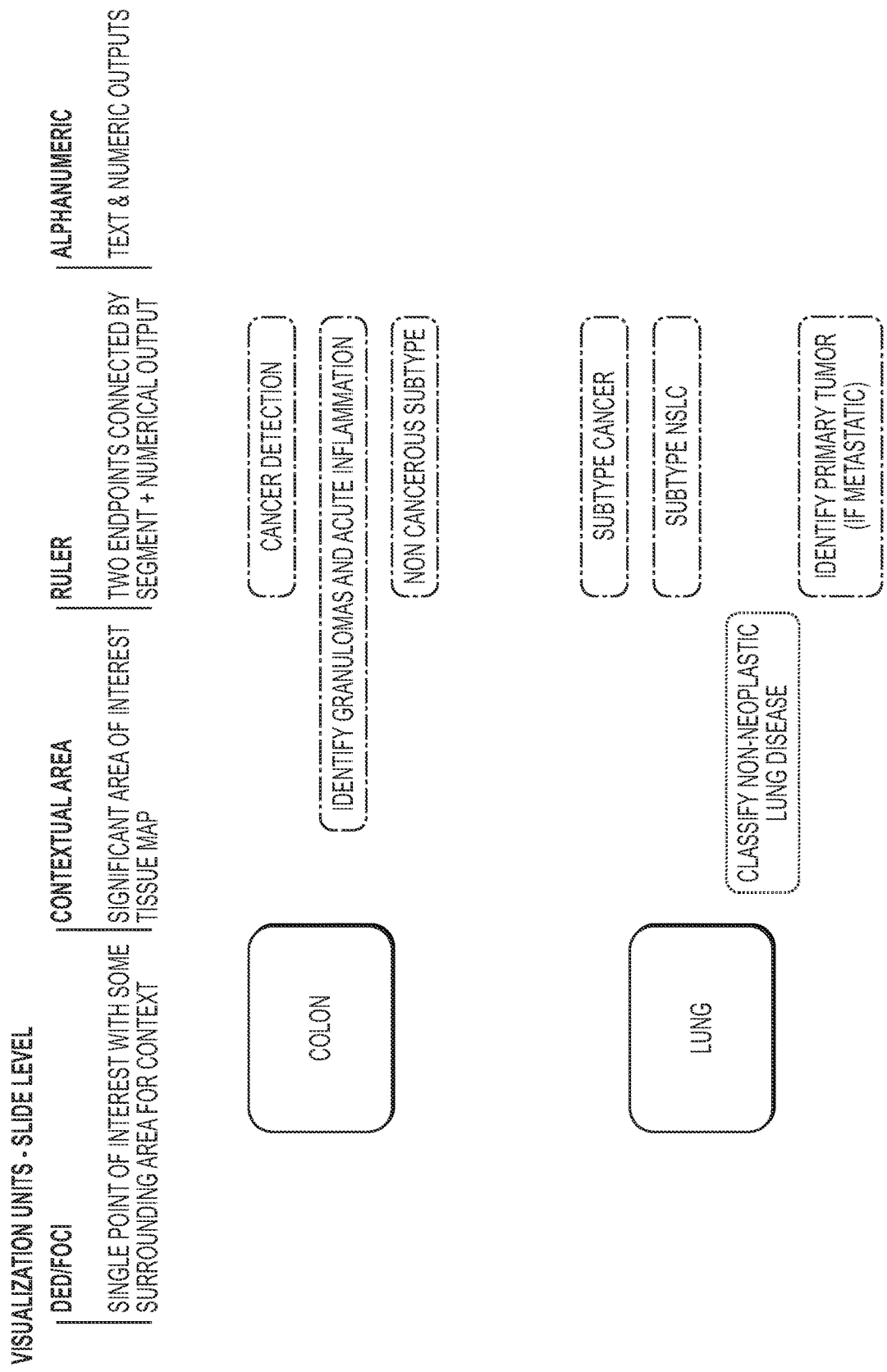

FIG. 6B shows an example visualization of a breast tissue specimen. As in FIG. 6A, foci areas are selected, measured and alphanumeric outputs are obtained. Further examples of bladder, colon, and lung tissues are shown in FIGS. 6C and 6D.

FIG. 7 illustrates an exemplary diagram of reportable features, according to exemplary embodiments of the present disclosure. For example, for an invasive cancer feature, reportable characteristics may include a grade, including an indication of whether that grade is within a range considered well, moderate, or poor, as well as a length of a measured feature. A resulting resection indicator may direct a user to only resection the tissue specimen margins. FIG. 7 includes a variety of other exemplary reportable features, but more details are described in Tables 3-6 below.

Figure 8:
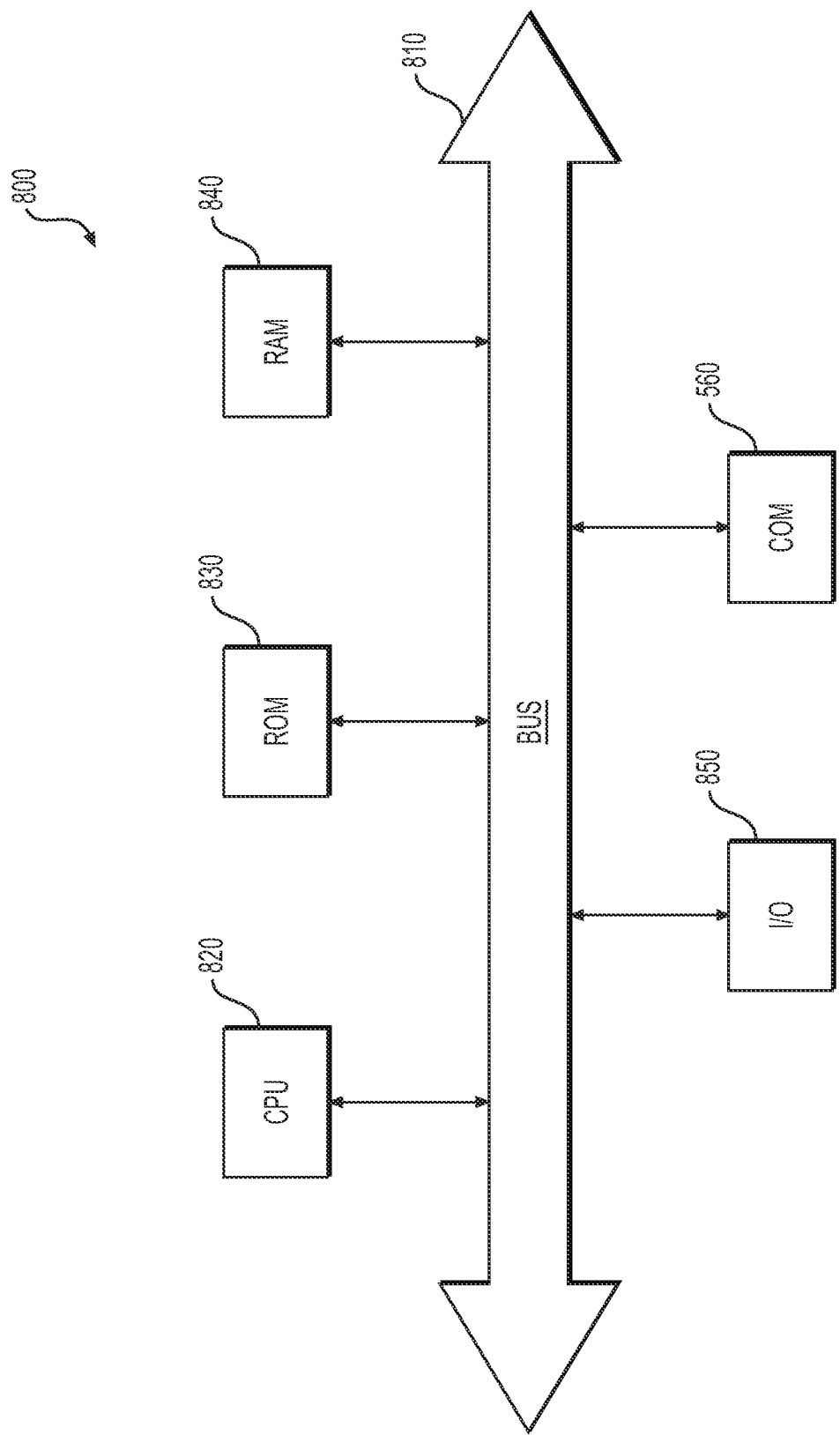
FIG. 8 illustrates an exemplary system that may execute techniques presented herein.

As shown in FIG. 8, device 800 may include a central processing unit (CPU) 820. CPU 820 may be any type of processor device, including, for example, any type of special purpose or a general-purpose microprocessor device. As will be appreciated by persons skilled in the relevant art, CPU 820 may also be a single processor in a multi-core/multi-processor system, such system operating alone, or in a cluster of computing devices operating in a cluster or server farm. CPU 820 may be connected to a data communication infrastructure 810, for example a bus, message queue, network, or multi-core message-passing scheme.

Device 800 may also include a main memory 840, for example, random access memory (RAM), and also may include a secondary memory 830. Secondary memory 830, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, a magnetic tape, an optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 830 may include similar means for allowing computer programs or other instructions to be loaded into device 800. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 800.

Device 800 may also include a communications interface ("COM") 860. Communications interface 860 allows software and data to be transferred between device 800 and external devices. Communications interface 860 may include a modem, a network interface (such as an Ethernet card), a communications port, a PCMCIA slot and card, or the like. Software and data transferred via communications interface 860 may be in the form of signals, which may be electronic, electromagnetic, optical, or other signals capable of being received by communications interface 860. These signals may be provided to communications interface 860 via a communications path of device 800, which may be implemented using, for example, wire or cable, fiber optics, a phone line, a cellular phone link, an RF link or other communications channels.

The hardware elements, operating systems and programming languages of such equipment are conventional in nature, and it is presumed that those skilled in the art are adequately familiar therewith. Device 800 may also include input and output ports 850 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically can be grouped together to perform a function or group of related functions. Like reference numerals are generally intended to refer to the same or similar components. Components and modules may be implemented in software, hardware or a combination of software and hardware.

The tools, modules, and functions described above may be performed by one or more processors. "Storage" type media may include any or all of the tangible memory of the computers, processors, or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and exemplar are to be considered exemplary only.

TABLE 3

1. Prostate AI Features

| Reportable Feature | Visualization type | Interaction type |
|---|---|---|
| Total Tumor | Tissue Map | Aggregate |
| Tumor percentage | Numeric output | |
| Tumor Length | Ruler | |
| | Numeric output | |
| Grade | Tissue Map | Aggregate |
| Grade Name | Text output (ex: grade 3) | |
| Grade percentage | Numeric output | |
| Gleason Score | Text output | |
| Gleason Grade | Numeric output | |

TABLE 4

2. Breast AI Features

| Reportable Feature | Visualization type | Interaction Type | Details | Part Level Reporting |
|---|---|---|---|---|
| IDC | Tissue Map | Aggregate | | Larger tumor evaluated, Presence |
| IDC Grade | Text output | | | Aggregate: One grade per part (average?) |
| Length of IDC | Ruler Numeric output | | | |
| Margins | | | | |
| ILC | Tissue Map | | | Larger tumor evaluated |
| ILC Grade | Text output | | | |
| Length of IDC | Ruler Numeric output | | | |
| DCIS | Tissue Map | Tissue Hop | | Number of slides with DCIS |
| DCIS Grade | Text output | | | |
| DCIS Architecture | Text output | | | Presence of architecture types |
| Comedonecorosis | Text output | | | |
| Margins | Ruler | Tissue hop | Maybe resection only | |
| Number of slides with DCIS | alphanumeric | | Maybe resection only | |
| LCIS | Tissue Map | Tissue Hop | | |
| LCIS Subtype | Text output | | | |
| Margins (maybe only for pleomorphic) | Ruler | Tissue hop | Maybe resection only | |
| ADH | Tissue Map | Aggregate | | |
| ALH | Tissue Map | Aggregate | | |
| Misc Atypia | Tissue Map | Aggregate | | |
| Calcification | Focus | Tissue hop | | Presence, Presence within IDC, DCIS, others? |
| Lymphovasular Invasion | Focus | Tissue hop | May require display of vessel + surrounding cancer cells | Presence |

TABLE 4-continued

2. Breast AI Features

| Reportable Feature | Visualization type | Interaction Type | Details | Part Level Reporting |
|---|---|---|---|---|
| Perineural Invasion | Focus | Tissue hop | May require display of nerve + surrounding cancer cells | Presence |
| Micro-invasion | Focus | Tissue hop | May require display of DCIS + surrounding microinvasive cancer | Presence Resection (count) |
| Biomarkers | Alphanumeric output | | | Some done in the diagnostic process (IHCs) some not (just sent along to oncologist)- like a PDFs- would just be attacked (oncotype, mamma print) |

TABLE 5

3. Bladder AI Features

| Reportable Feature | Visualization type(s) | Details | Interaction Type |
|---|---|---|---|
| PUNLMP/ UPUMP | Context area | | Aggregate |
| Papillary | Focus/context area | size of area dictates visualization type | |
| Papillary Grade | Alphanumeric | High or low grade | |
| Flat | Focus/context area | size of area dictates visualization type Grade metadate but might be always high grade | |
| Invasion lamina propria vs muscularis propria subtype | Focus/context area | size of area dictates visualization type | |
| LVI | Focus | May require display of vessel + surrounding cancer cells | Tissue hop |
| Mitoses? Muscularis Propria | Focus Context area | Maybe biopsies only (maybe not cancer-feature of tissue similar to calc in breast biopsy workflow) | Gallery Aggregate |

TABLE 6

| Possibly required Reporting Elements (RRE) | Breast Biopsy - Malignant | | Prostate Biopsy - Malignant | | Visualization Details | | |
|---|---|---|---|---|---|---|---|
| | Organ specific Descriptor | Details redisplay | Organ specific Descriptor | Details redisplay | Display Type | Display Details | Interaction |
| Invasive Cancer presence | Detection of any invasive malignancy on the slide | Possible minimum DED (if applicable): cluster of glands/cells, or cluster of invasive cells around in situ carcinoma | Detection of any invasive malignancy on the slide | Possible minimum DED (if applicable): cluster of glands/cells | DED Contextual | XY coordinate(s) Heatmap/tissue map/ tissue map alternative | |
| Invasive Cancer type(s) | Distinction between invasive lobular vs ductal carcinoma | Perhaps the outline of cancer can be color coded? | Detection of invasive acinar adenocarcinoma vs other cancers | Perhaps the outline of cancer can be color coded? | DED Contextual | Consider only contextual? Tissue Map (or alternative) per cancer type | |
| Invasive Cancer size | Measurement of largest focus of cancer in one core | Linear measurement may be shown over longest contiguous cancer area in one core | Measurement of all cancer 'foci' (predefined linear measurement of intervening normal tissue) | Linear measurement shown over a) foci of cancer through the long axis on the core, b) total tissue on slide the outline of cancer grad ecan be color coded? | Contextual | % and mm value in the analyze panel Display corresponding to the value (linear only?) on slide | |
| Invasive cancer grade | Segmentation of cancer by N-MSBR grade | Options: Probability of each score listed with ability to 'turn on' a visualization for explanation+ | Segmentation of cancer by Gleason grade | | Contextual | Tissue Map (or alternative) per grade | Same as invasive cancer type? OR Just a corresponding textual value to the invasive cancer subtype contextual display Grade based on mitotic count, tubule %, nuclei |

TABLE 6-continued

| Possibly required Reporting Elements (RRE) | Breast Biopsy - Malignant | | Prostate Biopsy - Malignant | | Visualization Details | | |
|---|---|---|---|---|---|---|---|
| | Organ specific Descriptor | Details redisplay | Organ specific Descriptor | Details redisplay | Display Type | Display Details | Interaction |
| In situ cancer presence | Detection of any in situ malignancy on the slide | Possible minimum DED: entire gland or glandular cluster that shows in situ carcinoma | consider intraductal carcinoma in this category | Possible minimum DED: entire gland that shows intraductal carcinoma | DED | XY coordinate? Box? Circle? | |
| In situ Cancer type(s) | Distinction between in situ lobular or ductal carcinoma | Contextual: Perhaps the outline of cancer can be color coded? | N/A | | Contextual | Tissue Map (or alternative) per type of in situ cancer | Same as invasive cancer type? OR Just a corresponding textual value to the invasive cancer subtype contextual display |
| In situ Cancer size | N/A | | N/A | | | | |
| In situ Cancer invasion locus | Detection of microinvasive foci | Possible minimum DED: cluster of invasive cells around in situ carcinoma | N/A | | DED | Display if microinvasive foci are detected | Same as in situ cancer presence? |
| In situ cancer grade | Segmentation of in situ carcinoma by grade | Options: Probability of overall grade with ability to 'turn on' a visualization for explanation | N/A | | Contextual | Tissue Map (or alternative) per grade of in situ cancer | Same as invasive cancer type? |
| Perineural invasion | N/A | Might not be required | Detection of foci of perineural invasion | Possible minimum DED: Nerve + cancer cells | DED | Nerve + cancer cells | Same as in situ cancer presence? |
| Lymphovascular invasion | Detection of foci of lymphovascular invasion | Possible minimum DED: Cancer Cells + within vascular space | Detection of foci of lymphovascular invasion | Possible minimum DED: Cancer Cells + within vascular space | DED | Cancer Cells + within vascular space | Same as in situ cancer presence? |
| Other high risk/ reportable lesion | Detection of predefined list of lesions# | Possible minimum DED: depends on lesion | HGPIN | Possible minimum DED: Glandular outline of gland with HGPIN | DED and/or contextual? | | |
| Misc - | Quantify mitosis | | N/A | | Contextual? | 1 × 1 mm box? | |
| Calcifications | Detection of calcifications | Possible minimum DED: granule of calcification in stroma, cells, etc. [just need to find one example of all areas where it is] | N/A | | DED | | Same as in situ cancer presence? |

What is claimed is:

1. A computer-implemented method of using at least one machine learning model to categorize a sample in digital pathology, comprising:
   receiving one or more cases, each associated with digital images of a pathology specimen, at a digital storage device;
   identifying, using the machine learning model, a case of the one or more cases as ready to view;
   receiving a selection of the case, the case comprising a plurality of parts;
   determining, using the machine learning model, a plurality of features based on the digital images associated with the case;
   automatically aggregating, using the machine learning model, a plurality of portions of the pathology specimen into a part index;
   determining a diagnosis based on the determined plurality of features, the diagnosis including the part index;
   determining, using the machine learning model, a plurality of partial reports using the plurality of features; and
   aggregating, the plurality of partial reports into a report, the report including the diagnosis.

2. The computer-implemented method of claim 1, wherein identifying a case as ready to view comprises verifying that all slides within the case are processed and uploaded to a digital storage device.

3. The computer-implemented method of claim 1, further comprising:
   determining, using the machine learning model, whether the plurality of parts are suspicious or non-suspicious;
   receiving a selection of a part of the plurality of parts;
   determining whether a plurality of slides associated with the part are suspicious or non-suspicious;
   determining, using the machine learning model, a collection of suspicious slides, of the plurality of slides, the machine learning model having been trained by processing a plurality of training images; and
   annotating the collection of suspicious slides and/or generating the report based on the collection of suspicious slides.

4. The computer implemented method of claim 3, wherein annotating the collection of suspicious slides further comprises:
   outlining at least one region around suspicious tissue;
   measuring a length and/or an area of the suspicious tissue; and
   outputting an annotation onto the collection of suspicious slides.

5. The computer-implemented method of claim 3, further comprising:
   populating the report with information about the collection of suspicious slides; and
   outputting the report to a user.

6. The computer-implemented method of claim 5, wherein information about the collection of suspicious slides comprises a focus area, a contextual area, one or more measurements of suspicious tissue, and/or an alphanumeric output.

7. The computer-implemented method of claim 6, wherein the alphanumeric output comprises a binary indication of a presence of one or more biomarkers within the tissue.

8. The computer-implemented method of claim 5, wherein the report and/or visualization of a suspicious tissue comprises a detection panel, a quantification panel, and/or an annotation log.

9. The computer-implemented method of claim 8, wherein the annotation log is searchable at a case level and at a part level.

10. The computer-implemented method of claim 1, further comprising:
    determining a complexity associated with each of the one or more cases; and
    prioritizing the one or more cases based on the determined complexity.

11. The computer-implemented method of claim 1, further comprising:
    sorting and/or filtering for display, using the machine learning model, the plurality of parts based on the determination of whether the plurality of parts are suspicious or non-suspicious.

12. The computer-implemented method of claim 1, further comprising:
    determining a pathology type; and
    generating the report based on the determined pathology type.

13. A system for using at least one machine learning model to categorize a sample in digital pathology, the system comprising:
    at least one memory storing instructions; and
    at least one processor configured to execute the instructions to perform operations comprising:
      receiving one or more cases, each associated with digital images of a pathology specimen, at a digital storage device;
      identifying, using the machine learning model, a case of the one or more cases as ready to view;
      receiving a selection of the case, the case comprising a plurality of parts;
      determining, using the machine learning model, a plurality of features based on the digital images associated with the case;
      automatically aggregating, using the machine learning model, a plurality of portions of the pathology specimen into a part index;
      determining a diagnosis based on the determined plurality of features, the diagnosis including the part index;
      determining, using the machine learning model, a plurality of partial reports using the plurality of features; and
      aggregating, the plurality of partial reports into a report, the report including the diagnosis.

14. The system of claim 13, wherein identifying a case as ready to view comprises verifying that all slides within the case are processed and uploaded to a digital storage device.

15. The system of claim 13, wherein the operations further comprise:
    determining, using the machine learning model, whether the plurality of parts are suspicious or non-suspicious;
    receiving a selection of a part of the plurality of parts;
    determining whether a plurality of slides associated with the part are suspicious or non-suspicious;
    determining, using the machine learning model, a collection of suspicious slides, of the plurality of slides, the machine learning model having been trained by processing a plurality of training images; and
    annotating the collection of suspicious slides and/or generating a report based on the collection of suspicious slides.

16. The system of claim 15, wherein annotating the collection of suspicious slides further comprises:
   outlining at least one region around suspicious tissue;
   measuring a length and/or an area of the suspicious tissue; and
   outputting an annotation onto the collection of suspicious slides.

17. The system of claim 16, wherein the operations further comprise:
   populating the report with information about the collection of suspicious slides; and
   outputting the report to a user, wherein information about the collection of suspicious slides comprises a focus area, a contextual area, one or more measurements of the suspicious tissue, and/or an alphanumeric output.

18. The system of claim 13, wherein the operations further comprise:
   determining a complexity associated with each of the one or more cases; and
   prioritizing the one or more cases based on the determined complexity.

19. A non-transitory computer-readable medium storing instructions that, when executed by a processor, perform a method of using at least one machine learning model to output a task-specific prediction, the method comprising:
   receiving one or more cases, each associated with digital images of a pathology specimen, at a digital storage device;
   identifying, using the machine learning model, a case of the one or more cases as ready to view;
   receiving a selection of the case, the case comprising a plurality of parts;
   determining, using the machine learning model, a plurality of features based on the digital images associated with the case;
   automatically aggregating, using the machine learning model, a plurality of portions of the pathology specimen into a part index;
   determining a diagnosis based on the determined plurality of features, the diagnosis including the part index;
   determining, using the machine learning model, a plurality of partial reports using the plurality of features; and
   aggregating, the plurality of partial reports into a report, the report including the diagnosis.

20. The non-transitory computer-readable medium of claim 19, the method further comprising:
   determining, using the machine learning model, whether the plurality of parts are suspicious or non-suspicious;
   receiving a selection of a part of the plurality of parts;
   determining whether a plurality of slides associated with the part are suspicious or non-suspicious;
   determining, using the machine learning model, a collection of suspicious slides, of the plurality of slides, the machine learning model having been trained by processing a plurality of training images; and
   annotating the collection of suspicious slides and/or generating a report based on the collection of suspicious slides by:
      outlining at least one region around suspicious tissue;
      measuring a length and/or an area of the suspicious tissue; and
      outputting an annotation onto the collection of suspicious slides.

* * * * *